(12) United States Patent
Ford et al.

(10) Patent No.: US 8,304,417 B2
(45) Date of Patent: Nov. 6, 2012

(54) CRYSTALLINE FORMS OF 4-(6-CHLORO-2,3-METHYLENEDIOXYANILINO)-7-[2-(4-METHYLPIPERAZIN-1-YL)ETHOXY]-5-TETRAHYDROPYRAN-4-YLOXYQUINAZOLINE

(75) Inventors: James Gair Ford, Macclesfield (GB); James Francis McCabe, Macclesfield (GB); Anne O'Kearney-McMullan, Macclesfield (GB); Simon Mark Pointon, Macclesfield (GB); Lyn Powell, Macclesfield (GB); Philip O'Keefe, Loughborough (GB); Mark Purdie, Loughborough (GB); Jane Withnall, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 1254 days.

(21) Appl. No.: 11/793,064

(22) PCT Filed: Dec. 14, 2005

(86) PCT No.: PCT/GB2005/004807
§ 371 (c)(1),
(2), (4) Date: Apr. 1, 2008

(87) PCT Pub. No.: WO2006/064217
PCT Pub. Date: Jun. 22, 2006

(65) Prior Publication Data
US 2009/0099196 A1    Apr. 16, 2009

(30) Foreign Application Priority Data
Dec. 17, 2004   (GB) .................................. 0427697.8

(51) Int. Cl.
*A01N 43/90*     (2006.01)
*A61K 31/519*    (2006.01)
*C07D 487/00*    (2006.01)

(52) U.S. Cl. .................................. 514/259.31; 544/263

(58) Field of Classification Search .................. None
See application file for complete search history.

(56) References Cited

U.S. PATENT DOCUMENTS

| 7,049,438 | B2 | 5/2006 | Hennequin et al. |
| 7,115,615 | B2 | 10/2006 | Hennequin et al. |
| 7,141,577 | B2 | 11/2006 | Ple |

FOREIGN PATENT DOCUMENTS

| WO | WO 01/94341 |   | 12/2001 |
| WO | WO0194341 | * | 12/2001 |
| WO | WO 02/16352 |   | 2/2002 |
| WO | WO 02/085895 |   | 10/2002 |
| WO | WO 2004/041829 |   | 5/2004 |
| WO | WO 2004/043472 |   | 5/2004 |
| WO | WO 2004/087120 |   | 10/2004 |
| WO | WO 2004/096226 |   | 11/2004 |
| WO | WO 2004/098604 |   | 11/2004 |

OTHER PUBLICATIONS

Berge, et. al., Journal of Pharmaceutical Sciences, (1977), 66(1), pp. 1-19.*
http://www.polmon.com/images/pdf/automation/crystallization.pdf, last accessed on Mar. 13, 2012.*
http://www.dafratec.com/pdf/crysta116_Polymorph_and_Salt.pdf, last accessed on Mar. 13, 2012.*

* cited by examiner

*Primary Examiner* — Jeffrey Murray
(74) *Attorney, Agent, or Firm* — Morgan, Lewis & Bockius LLP

(57) ABSTRACT

The present invention relates to chemical processes useful in the manufacture of the compound 4-(6-chloro-2,3-methylenedioxyanilino)-7-[2-(4-methylpiperazin-1-yl)ethoxy]-5-tetrahydropyran-4-yloxyquinazoline (the active entity within AZD0530), to intermediates useful in the manufacture of that compound and to processes for the manufacture of those intermediates. The invention also relates to particular crystalline forms of that compound such as a difumarate salt and a trihydrate and to pharmaceutical compositions containing such crystalline forms.

18 Claims, 3 Drawing Sheets

Figure 1    XRPD Pattern for crystalline AZD0530 Difumarate
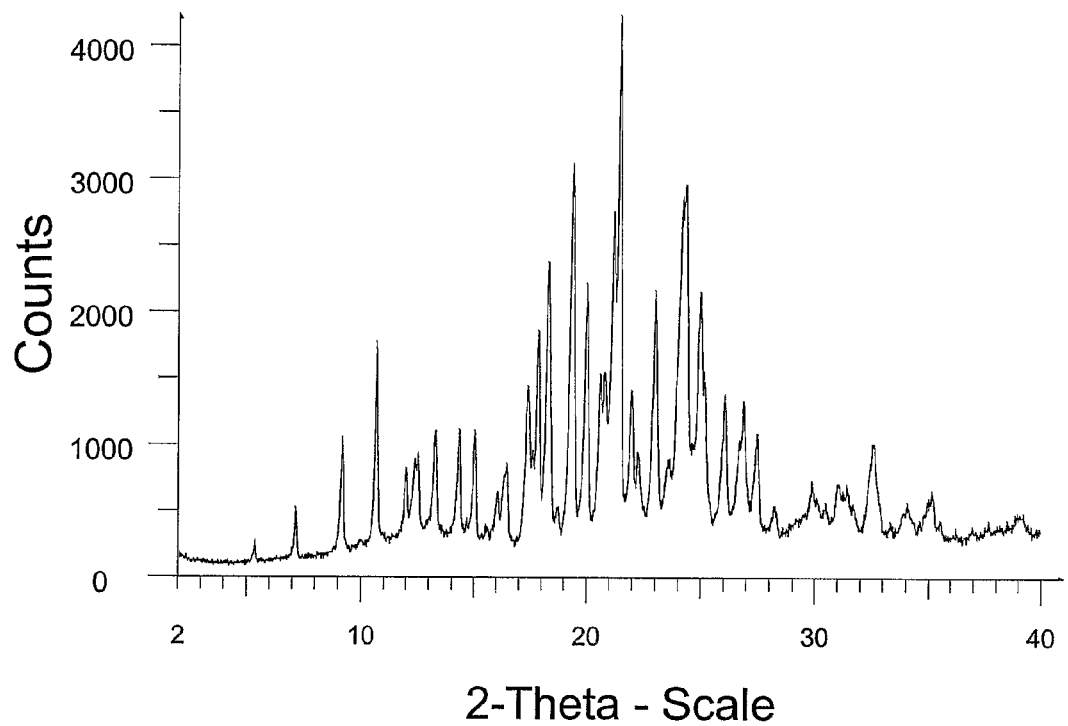
Figure 2    XRPD Pattern for crystalline AZD0530 Sesquifumarate tetrahydrate
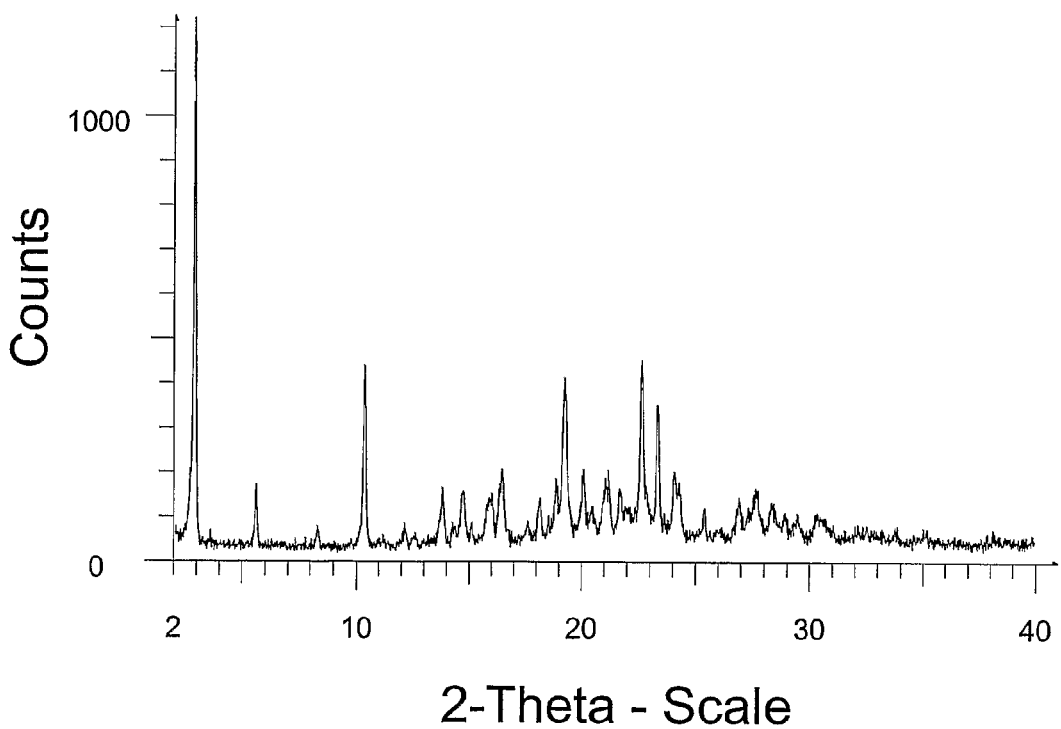

Figure 3    XRPD Pattern for crystalline AZD0530 trihydrate
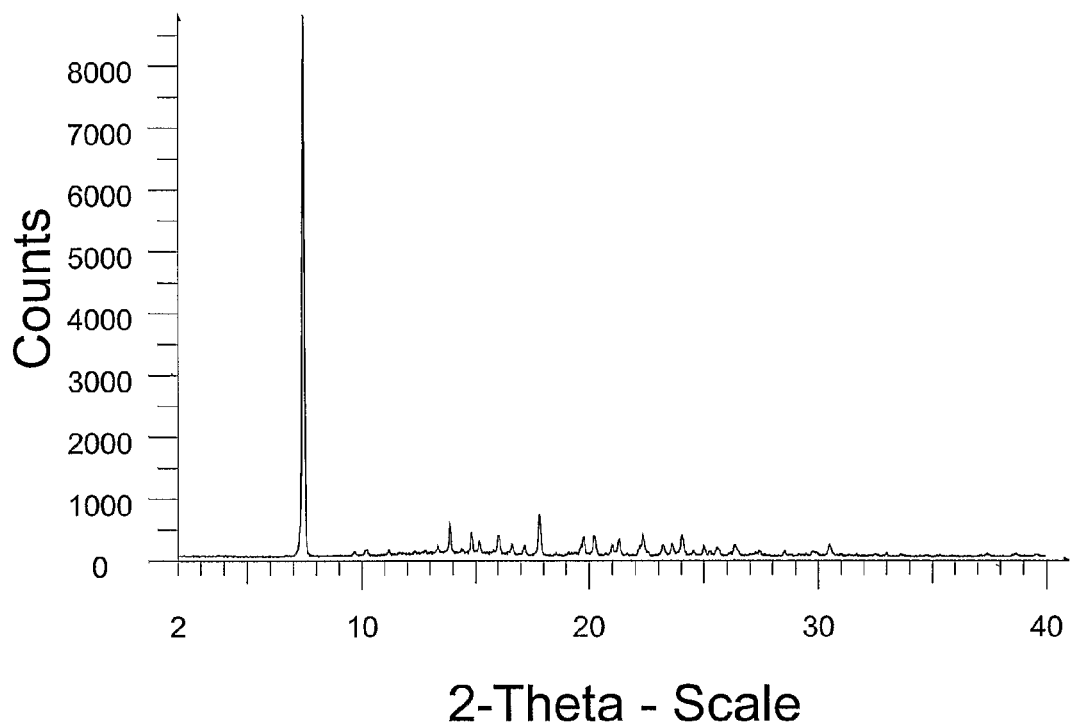
Figure 4    XRPD Pattern for crystalline anhydrous AZD0530
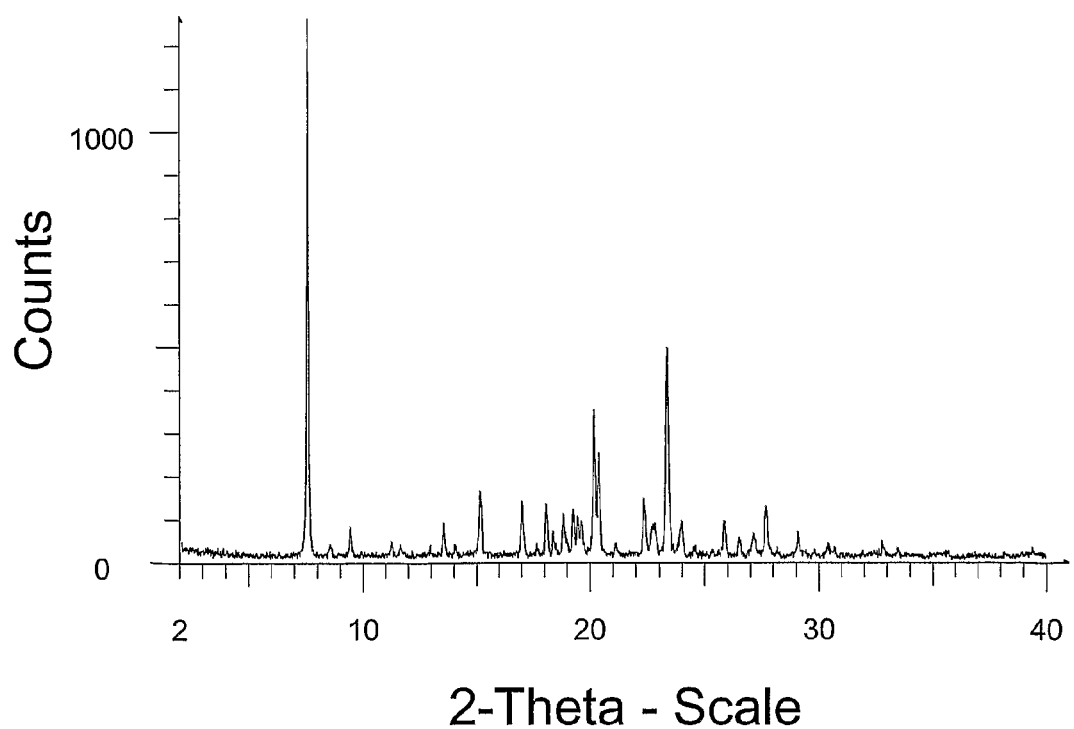

Figure 5    DRIFT scan for AZD0530 Difumarate
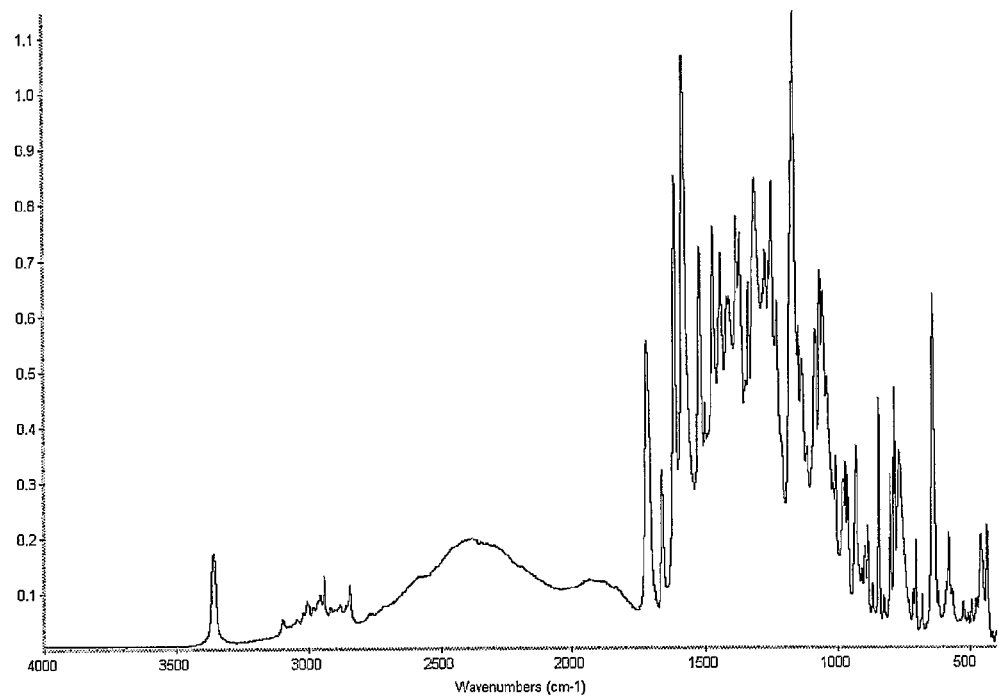
Figure 6    DRIFT scan for AZD0530 Sesquifumarate Tetrahydrate
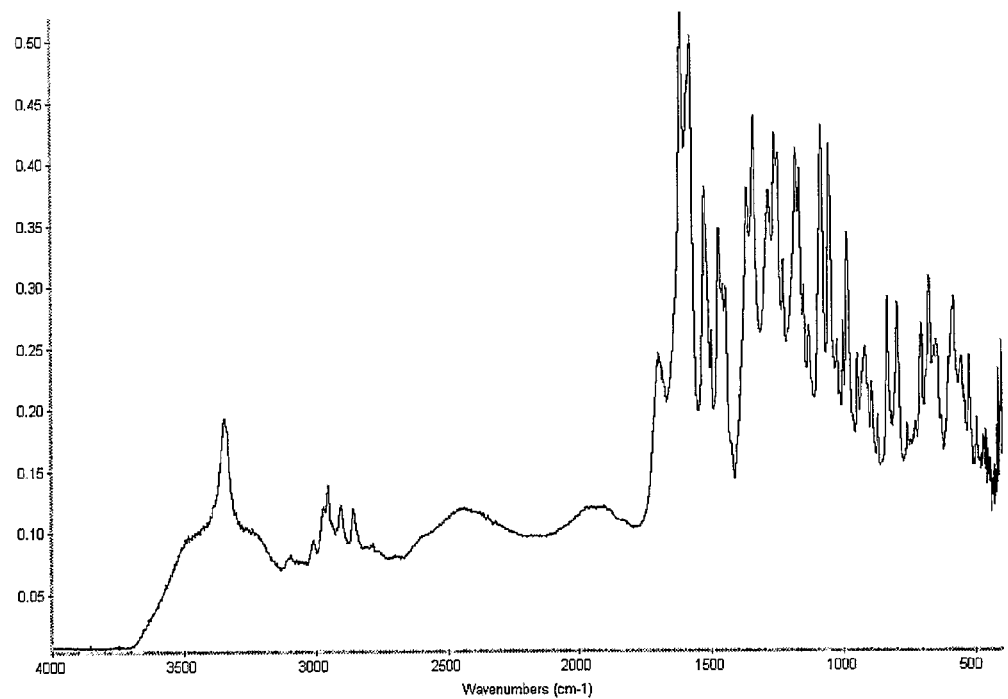

CRYSTALLINE FORMS OF 4-(6-CHLORO-2,3-METHYLENEDIOXYANILINO)-7-[2-(4-METHYLPIPERAZIN-1-YL)ETHOXY]-5-TETRAHYDROPYRAN-4-YLOXYQUINAZOLINE

The present invention relates to improved chemical processes and intermediates useful in the manufacture of certain quinazoline derivatives, or pharmaceutically-acceptable salts thereof, which possess anti-tumour properties. The invention also relates to processes for the manufacture of said intermediates and to processes for the manufacture of such quinazoline derivatives utilising said intermediates. The invention also relates to particular crystalline forms of certain quinazoline derivatives and to particular crystalline pharmaceutically-acceptable salts thereof which each possess anti-tumour properties.

In particular, the present invention relates to chemical processes and intermediates useful in the manufacture of the compound 4-(6-chloro-2,3-methylenedioxyanilino)-7-[2-(4-methylpiperazin-1-yl)ethoxy]-5-tetrahydropyran-4-yloxyquinazoline which compound is disclosed as Compound No. 73 within the Table in Example 14 of International Patent Application WO 01/94341.

That compound is described herein by way of the Formula I

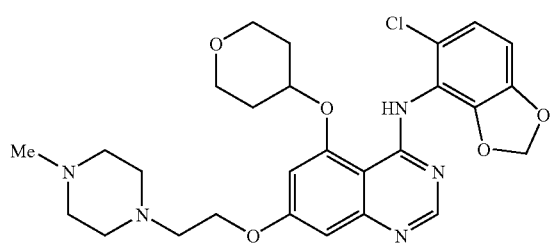

and as AZD0530, the code number by which the compound is known.

AZD0530 is an inhibitor of the Src family of non-receptor tyrosine kinase enzymes and, thereby, is a selective inhibitor of the motility of tumour cells and a selective inhibitor of the dissemination and invasiveness of mammalian cancer cells leading to inhibition of metastatic tumour growth. In particular, the compound AZD0530 is an inhibitor of c-Src non-receptor tyrosine kinase and should be of value as an anti-invasive agent for use in the containment and/or treatment of solid tumour disease in the human or animal body.

The route for preparing the compound of the Formula I that is disclosed in International Patent Application WO 01/94341 involves the reaction of the compound 4-(6-chloro-2,3-methylenedioxyanilino)-7-hydroxy-5-tetrahydropyran-4-yloxyquinazoline with an alkylating agent to form the 2-(4-methylpiperazin-1-yl)ethoxy side-chain at the 7-position. The product of the reaction is disclosed in WO 01/94341 in the form of a dihydrochloride salt and in the form of a free base.

This existing route is satisfactory for the synthesis of relatively small amounts of the compound of the Formula I but the route involves linear rather than convergent synthesis, requiring the multiple use of chromatographic purification steps and the isolation of a substantial number of intermediates. As such, the overall yield of the synthesis is not high. There is therefore a need for a more efficient synthesis of the compound of the Formula I suitable for use to make larger quantities of that compound. Preferably, the new synthesis should not involve costly and time-consuming chromatographic purification procedures.

According to the present invention, we have now devised suitable processes for the manufacture of AZD0530, the compound of the Formula I. The new processes are advantageous in that they allow the final product to be made in high quality and in satisfactory yield on a larger scale. The processes allow a substantial reduction in the number of intermediates that must be isolated and, in general, are more convergent than the previous routes. Such changes provide significant advantages of time and cost. Conveniently, chromatographic purification procedures are not required.

According to the invention, processes are also provided for the manufacture of key intermediates that may be used in the preparation of AZD0530.

According to a further aspect of the invention, particular crystalline forms of AZD0530 and particular crystalline pharmaceutically-acceptable salts thereof which each possess anti-tumour properties are also provided.

According to a first aspect of the present invention, there is provided a process for the manufacture of AZD0530, the compound of the Formula I

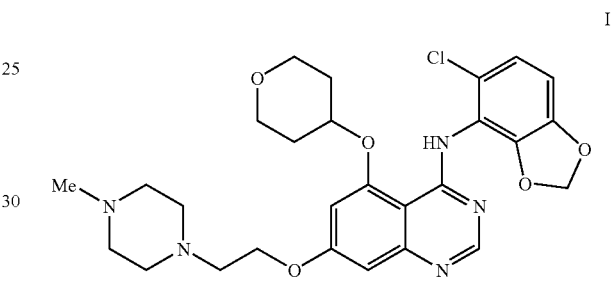

which comprises the reaction, conveniently in the presence of a suitable base, of a quinazoline of the Formula II

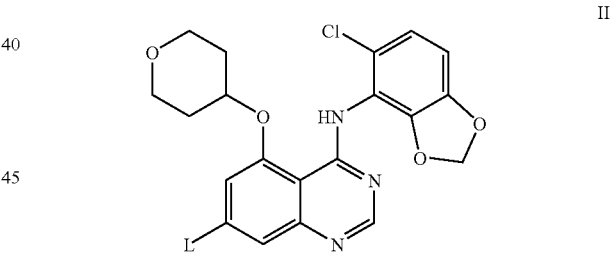

wherein L is a displaceable group and the NH functional group is protected if necessary, with 1-(2-hydroxyethyl)-4-methylpiperazine; whereafter any protecting group that is present is removed by conventional means; and whereafter the compound of the Formula I obtained in the form of the free base may be converted into a pharmaceutically-acceptable salt, and the compound of the Formula I obtained in the form of a salt may be converted into the free base, if necessary.

The reaction may conveniently be carried out in the presence of a suitable base, for example, an organic amine base such as, for example, pyridine, 2,6-lutidine, collidine, 4-dimethylaminopyridine, triethylamine, N-methylmorpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride, or, for example, an alkali or alkaline earth metal (1-12C)alkoxide, for example sodium or potassium tert-butoxide, sodium or potassium tert-pentoxide or sodium or potassium 3,7-dimethyloctoxide. Conveniently, a suitable base is, for example, an alkali metal hydroxide, for example sodium hydroxide or potassium hydroxide, or, for example, an alkali metal (1-6C) alkoxide, for example sodium or potassium tert-butoxide or sodium or potassium tert-pentoxide. More conveniently, a suitable base is, for example, an alkali metal (1-6C)alkoxide, for example sodium or potassium tert-butoxide or sodium or potassium tert-pentoxide.

A suitable displaceable group L is, for example, a halogeno, (1-6C)alkoxy, aryloxy or sulphonyloxy group, for example a fluoro, chloro, bromo, methoxy, ethoxy, phenoxy, pentafluorophenoxy, methanesulphonyloxy or toluene-4-sulphonyloxy group. Conveniently, the displaceable group L is a halogeno group. More conveniently, the displaceable group L is a fluoro group.

The reaction is conveniently carried out in the presence of a suitable inert solvent or diluent or a mixture of suitable inert solvents or diluents, for example in an optionally substituted di-(1-6C)alkyl ether or a cyclic alkyl ether such as dibutyl ether, methyl tert-butyl ether, di-(2-methoxyethyl)ether, 1,2-dimethoxyethane, 1,2-diethoxyethane, tetrahydrofuran or 1,4-dioxan, or a dipolar aprotic solvent such as N,N-dimethylformamide, N,N-dimethylacetamide, N-methylpyrrolidin-2-one or dimethylsulphoxide. Conveniently, a suitable inert solvent or diluent with a boiling point of greater than 50° C. is employed, for example, an optionally substituted di-(1-6C) alkyl ether such as di-(2-methoxyethyl)ether or 1,2-diethoxyethane.

The reaction is carried out at a temperature in the range, for example, 0 to 250° C., conveniently in the range 50 to 150° C., more conveniently in the range 75 to 130° C.

Conveniently, it is not necessary to protect the NH functional group. However, if it is desired to use a protecting group, such groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

Examples of protecting groups for the NH functional group include formyl, aryl-lower alkyl groups (for example benzyl and substituted benzyl such as 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for the removal of protecting groups for the NH functional group include, for example, acid-, base-, metal- or enzymically-catalysed hydrolysis for groups such as 2-nitrobenzyloxycarbonyl, hydrogenation for groups such as benzyl and photolysis for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, 2$^{nd}$ Edition, by T. Green et al., also published by John Wiley & Son, for general guidance on protecting groups.

The compound of Formula I may be obtained from this process in the form of the free base or alternatively it may be obtained in the form of an acid addition salt such as a hydrohalide salt. When it is desired to obtain the free base from the salt, the salt may be treated with a suitable base, for example, an organic amine base such as, for example, pyridine, 2,6-lutidine, collidine, 4-dimethylaminopyridine, triethylamine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide. When it is desired to obtain the compound of Formula I in the form of a pharmaceutically-acceptable salt, the free base form may be reacted with a suitable acid using a conventional procedure, for example to form an acid-addition salt with an inorganic or organic acid such as hydrochloric, hydrobromic, sulphuric, trifluoroacetic, citric or maleic acid.

Quinazoline starting materials of the Formula II wherein L is a displaceable group as defined hereinbefore may be obtained by conventional procedures such as those disclosed in International Patent Application WO 01/94341. In particular, a quinazoline starting material of the Formula II wherein L is a fluoro group may be obtained by conventional procedures such as those disclosed in International Patent Application WO 01/94341, for example for the preparation of Compound No. 5 within the Table in Example 4.

According to a further feature of the invention, there is provided a process for the manufacture of a quinazoline of the Formula III

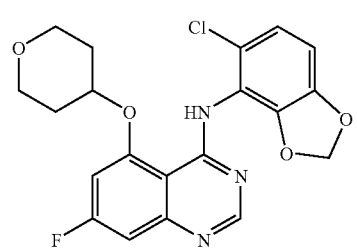

which comprises:—
(a) the reaction, conveniently in the presence of a suitable base, of a quinazolinone of the Formula IV

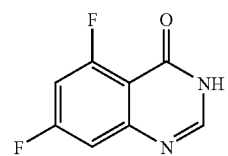

with an activating agent to form a quinazoline of the Formula V

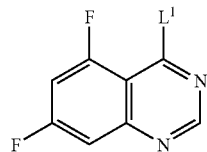

wherein $L^1$ is a displaceable group;
(b) the displacement reaction, conveniently in the presence of a suitable base, of the quinazoline of the Formula V with 6-chloro-2,3-methylendioxyaniline to form a quinazoline of the Formula VI

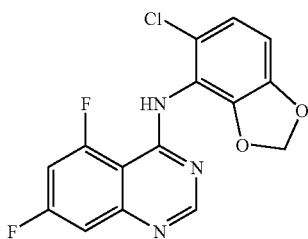

whereafter the compound of the Formula VI obtained in the form of the free base may be converted into a salt, and the compound of the Formula VI obtained in the form of a salt may be converted into the free base; and
(c) the reaction, conveniently in the presence of a suitable base, of the quinazoline of the Formula VI with 4-hydroxytetrahydropyran to form a quinazoline of the Formula III, whereafter the compound of the Formula III obtained in the form of the free base may be converted into a salt, and the compound of the Formula III obtained in the form of a salt may be converted into the free base.

For process step (a), a suitable activating agent that will form a leaving group $L^1$ is, for example, a phosphoryl halide such as phosphoryl chloride or phosphoryl bromide, or a halogenating agent such as thionyl chloride or the halogenating agent formed by a mixture of carbon tetrachloride and triphenylphosphine or the halogenating agent formed by a mixture of carbon tetrabronide and triphenylphosphine. Alternatively, any 4-haloquinazoline so obtained may be converted, if required, into a 4-pentafluorophenoxyquinazoline by reaction with pentafluorophenol in the presence of a suitable base such as potassium carbonate and in the presence of a suitable solvent such as N,N-dimethylformamide. A suitable base that may be used during process step (a) is, for example, an organic amine base such as, for example, pyridine, 2,6-lutidine, collidine, 4-dimethylaminopyridine, triethylamine, diisopropylethylamine, N-methylmorpholine or diazabicyclo[5.4.0]undec-7-ene. A suitable solvent or diluent for process step (a) is, for example, an aromatic solvent such as toluene, a xylene, cumene, chlorobenzene, anisole or phenetole. A further suitable solvent or diluent is a polar aprotic solvent such as acetonitrile, propionitrile, butyronitrile, ethyl acetate, tetrahydrofuran or 1,4-dioxan or a dipolar aprotic solvent such as N,N-dimethylformamide, N,N-dimethylacetamide, N-methylpyrrolidin-2-one or dimethylsulphoxide. A further suitable solvent or diluent is water or a polar protic solvent such as a primary, secondary or tertiary (1-6C)alkyl alcohol, for example, methanol, ethanol, a butanol or pentanol. Mixtures of such suitable solvents or diluents may be used. The reaction may be carried out at a temperature in the range, for example, 10 to 250° C., conveniently in the range 40 to 160° C.

Conveniently for process step (a), a suitable activating agent is, for example, a phosphoryl halide such as phosphoryl chloride and the reaction is carried out in the presence of an organic amine base such as triethylamine or diisopropylethylamine, using a solvent or diluent such as toluene, chlorobenzene, anisole or acetonitrile, and at a temperature in the range 70 to 160° C., more conveniently in the range 70 to 120° C.

The displacement reaction of process step (b) may be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, diisopropylethylamine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride.

The displacement reaction is conveniently carried out in the presence of a suitable inert solvent or diluent, for example a primary, secondary or tertiary (1-6C)alkyl alcohol such as isopropanol, sec-butanol or tert-butanol, a halogenated solvent such as methylene chloride, chloroform or carbon tetrachloride, an aromatic solvent such as toluene, a xylene, cumene, chlorobenzene, anisole or phenetole, a polar aprotic solvent such as acetonitrile, propionitrile, butyronitrile, ethyl acetate, tetrahydrofuran or 1,4-dioxan or a dipolar aprotic solvent such as N,N-dimethylformamide, N,N-dimethylacetamide, N-methylpyrrolidin-2-one or dimethylsulphoxide. Mixtures of such suitable solvents or diluents may be used. The reaction is conveniently carried out at a temperature in the range, for example, 10 to 250° C., suitably in the range 40 to 160° C., more conveniently in the range 70 to 120° C.

Typically, the displacement reaction of process step (b) may be carried out in the presence of a protic solvent such as isopropanol and at a temperature in the range, for example, 25 to 150° C., conveniently at or near the reflux temperature of the reaction solvent. Optionally, the displacement reaction may be carried out in the presence of an acid, for example hydrogen chloride gas in diethyl ether or the hydrogen chloride formed when the compound of the Formula IV is reacted with an activating agent that is a halogenating agent such as thionyl chloride or phosphoryl chloride.

For process step (c), the reaction may conveniently be carried out in the presence of a suitable base, for example, an organic amine base such as, for example, pyridine, 2,6-lutidine, collidine, 4-dimethylaminopyridine, triethylamine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride, or, for example, an alkali or alkaline earth metal (1-12C)alkoxide, for example sodium or potassium tert-butoxide, sodium or potassium tert-pentoxide or sodium or potassium 3,7-dimethyloctoxide. Conveniently, a suitable base is, for example, an alkali metal hydroxide, for example sodium hydroxide or potassium hydroxide, or, for example, an alkali metal (1-6C)alkoxide, for example sodium or potassium tert-butoxide, sodium or potassium tert-pentoxide. More conveniently, a suitable base is, for example, an alkali metal (1-6C)alkoxide, for example sodium or potassium tert-butoxide or sodium or potassium tert-pentoxide.

For process step (c), the reaction is conveniently carried out in the presence of a suitable inert solvent or diluent or a mixture of suitable inert solvents or diluents, for example in an optionally substituted di-(1-6C)alkyl ether or a cyclic alkyl ether such as dibutyl ether, methyl tert-butyl ether, di-(2-methoxyethyl)ether, 1,2-dimethoxyethane, 1,2-diethoxyethane, tetrahydrofuran or 1,4-dioxan, or a dipolar aprotic solvent such as N,N-dimethylformamide, N,N-dimethylacetamide, N-methylpyrrolidin-2-one or dimethylsulphoxide. Conveniently, a suitable inert solvent or diluent with a boiling point of greater than 50° C. is employed, for example, a cyclic alkyl ether such as tetrahydropyran or a dipolar aprotic solvent such as N-methylpyrrolidin-2-one.

For process step (c), the reaction is carried out at a temperature in the range, for example, 0 to 250° C., conveniently in the range 25 to 125° C., more conveniently in the range 40 to 80° C.

More conveniently, the intermediate of the Formula V is not isolated as such but is used as a solution or slurry in an organic solvent. Thereby, the compound of the Formula VI may be manufactured from the compound of the Formula IV in a one-pot procedure. The conversion of the compound of the Formula IV into the compound of the Formula VI in this manner is illustrated hereinafter within Example 5. Yet more conveniently, the intermediate of the Formula V is formed in the presence of 6-chloro-2,3-methylendioxyaniline and reacts directly therewith in a one-pot procedure. The conversion of the compound of the Formula IV into the compound of the Formula VI in this manner is illustrated hereinafter within Example 7.

The quinazoline of the Formula VI is a novel compound that forms a further aspect of the present invention.

According to a further aspect of the invention, there is provided a process for the manufacture of AZD0530 which comprises steps (a) and (b) immediately above to manufacture the quinazoline of the Formula VI and its conversion as defined hereinbefore into AZD0530.

There is also provided an alternative process for the manufacture of a quinazoline of the Formula VI which comprises:—
(a) the reaction, conveniently in the presence of a suitable organometallic catalyst, of 2,4,6-trifluorobenzonitrile of the Formula VII

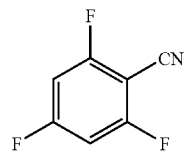

with 6-chloro-2,3-methylendioxyaniline to form an amidine of the Formula VIII

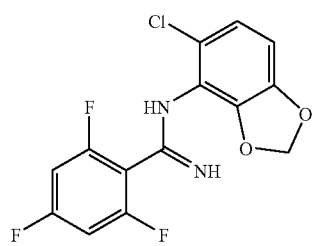

and (b) the reaction of the amidine of the Formula VIII with formamidine, or a salt thereof, to form a quinazoline of the Formula VI; whereafter the compound of the Formula VI obtained in the form of the free base may be converted into a salt, and the compound of the Formula VI obtained in the form of a salt may be converted into the free base.

For process step (a) immediately above, a suitable organometallic reagent is, for example, an organoaluminium compound such as trimethylaluminium, an organoiron compound such as diphenylphosphinoferrocene or an organopalladium compound such as tetrakis(triphenylphosphine)palladium (0). The reaction is conveniently carried out in the presence of a suitable inert solvent or diluent as defined hereinbefore. Conveniently, an aromatic solvent such as toluene or a xylene, cumene or chlorobenzene is used as reaction solvent. The reaction is conveniently carried out at a temperature in the range, for example, 10 to 250° C., suitably in the range 75 to 125° C.

For process step (b) immediately above, the reaction is conveniently carried out in the presence of a suitable inert solvent or diluent as defined hereinbefore, for example in an aromatic solvent such as toluene or a xylene, cumene, chlorobenzene, anisole or phenetole and at a temperature in the range, for example, 10 to 250° C., suitably in the range 75 to 125° C.

The conversion of the compound of the Formula VII into the compound of the Formula VI in this manner is illustrated hereinafter within Example 6.

There is also provided an alternative process for the manufacture of a quinazoline of the Formula III

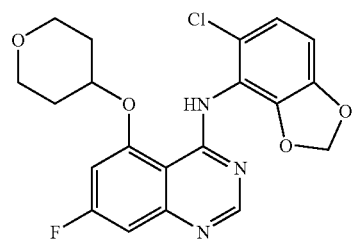

which comprises:—
(a) the reaction, conveniently in the presence of a suitable base as defined hereinbefore, of a quinazolinone of the Formula IV

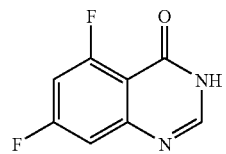

with 4-hydroxytetrahydropyran to form a quinazolinone of the Formula IX,

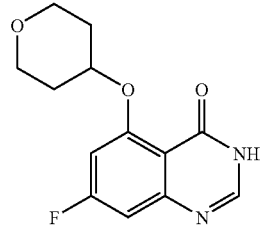

whereafter the compound of the Formula IX obtained in the form of the free base may be converted into a salt, and the compound of the Formula IX obtained in the form of a salt may be converted into the free base;

(b) the reaction, conveniently in the presence of a suitable base, of the quinazolinone of the Formula IX with an activating agent as defined hereinbefore to form a quinazoline of the Formula X

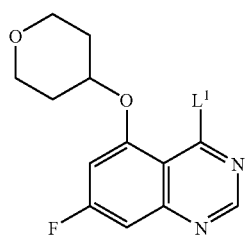

wherein $L^1$ is a displaceable group as described hereinbefore; and (c) the displacement reaction, conveniently in the presence of a suitable base, of the quinazoline of the Formula X with 6-chloro-2,3-methylendioxyaniline;

whereafter the compound of the Formula III obtained in the form of the free base may be converted into a salt, and the compound of the Formula III obtained in the form of a salt may be converted into the free base.

For process step (a) immediately above, the reaction may conveniently be carried out in the presence of a suitable base as defined for process step (c) above (relating to the manufacture of a quinazoline of the Formula III from a quinazoline of the Formula VI), in the presence of a suitable inert solvent or diluent or a mixture of suitable inert solvents or diluents, as defined for process step (c) above (relating to the manufacture of a quinazoline of the Formula III from a quinazoline of the Formula VI), and at a temperature in the range, for example, 0 to 250° C., conveniently in the range 25 to 125° C., more conveniently in the range 40 to 80° C.

For process step (b) immediately above, a suitable activating agent that will form a leaving group $L^1$ is, for example, a phosphoryl halide such as phosphoryl chloride or phosphoryl bromide, or a halogenating agent such as thionyl chloride or a halogenating agent formed by a mixture of carbon tetrachloride and triphenylphosphine or a halogenating agent formed by a mixture of carbon tetrabromide and triphenylphosphine. A suitable base that may be used during process step (b) immediately above is, for example, an organic amine base such as, for example, pyridine, 2,6-lutidine, collidine, 4-dimethylaminopyridine, triethylamine, diisopropylethylamine, N-methylmorpholine or diazabicyclo[5.4.0]undec-7-ene. A suitable solvent or diluent for process step (b) immediately above is, for example, an aromatic solvent such as toluene, a xylene, cumene, chlorobenzene, anisole or phenetole. A further suitable solvent or diluent is a polar aprotic solvent such as acetonitrile, propionitrile, butyronitrile, ethyl acetate, tetrahydrofuran or 1,4-dioxan or a dipolar aprotic solvent such as N,N-dimethylformamide, N,N-dimethylacetamide, N-methylpyrrolidin-2-one or dimethylsulphoxide. Mixtures of such suitable solvents or diluents may be used. The reaction may be carried out at a temperature in the range, for example, 10 to 250° C., conveniently in the range 40 to 120° C.

Conveniently for process step (b) immediately above, a suitable activating agent is, for example, a phosphoryl halide such as phosphoryl chloride and the reaction is carried out in the presence of an organic amine base such as triethylamine or diisopropylethylamine, using a solvent or diluent such as toluene, chlorobenzene or acetonitrile, and at a temperature in the range 70 to 100° C.

The displacement reaction of process step (c) immediately above may be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, diisopropylethylamine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride.

The displacement reaction of process step (c) immediately above is conveniently carried out in the presence of a suitable inert solvent or diluent, for example a primary, secondary or tertiary (1-6C)alkyl alcohol such as isopropanol, sec-butanol or tert-butanol, a halogenated solvent such as methylene chloride, chloroform or carbon tetrachloride, an aromatic solvent such as toluene, a xylene, cumene, chlorobenzene, anisole or phenetole, a polar aprotic solvent such as acetonitrile, propionitrile, butyronitrile, ethyl acetate, tetrahydrofuran or 1,4-dioxan or a dipolar aprotic solvent such as N,N-dimethylformamide, N,N-dimethylacetamide, N-methylpyrrolidin-2-one or dimethylsulphoxide. Mixtures of such suitable solvents or diluents may be used. The reaction is conveniently carried out at a temperature in the range, for example, 10 to 250° C., suitably in the range 40 to 120° C.

Conveniently, the intermediate of the Formula X is not isolated as such but is used as a solution or slurry in an organic solvent. Thereby, the compound of the Formula III may be manufactured from the compound of the Formula IX in a one-pot procedure. The conversion of the compound of the Formula IX into the compound of the Formula III in this manner is illustrated hereinafter within Example 8.

According to a further aspect of the invention, there is provided a process for the manufacture of AZD0530 which comprises step (a) immediately above to manufacture the quinazolinone of the Formula IX and its conversion as defined hereinbefore into AZD0530.

Necessary starting materials such as the quinazolinone of the Formula IV may be obtained by standard procedures of organic chemistry. The preparation of the quinazolinone of the Formula IV is described within the following representative Examples (Examples 1 and 2). Alternatively, such necessary starting materials are obtainable by analogous procedures to those illustrated which are within the ordinary skill of an organic chemist.

According to a further aspect of the present invention, there is provided a process for the manufacture of AZD0530, the compound of the Formula I

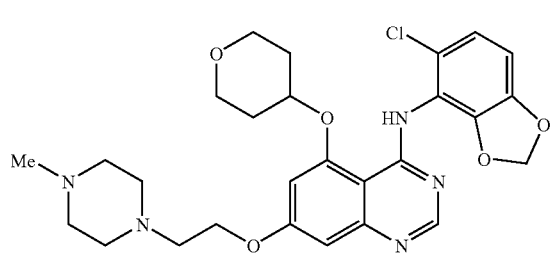

which comprises:—

(a) the reaction, conveniently in the presence of a suitable base as defined hereinbefore, of the quinazolinone of the Formula XI

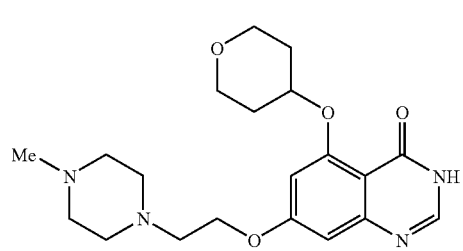

XI with an activating agent as defined hereinbefore to form a quinazoline of the Formula XII

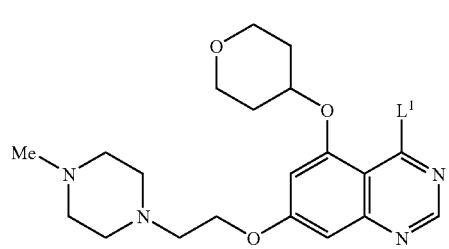

XII wherein L¹ is a displaceable group as described hereinbefore; and (b) the displacement reaction, conveniently in the presence of a suitable base as defined hereinbefore, of the quinazoline of the Formula XII with 6-chloro-2,3-methylendioxyaniline; whereafter the compound of the Formula I obtained in the form of the free base may be converted into a pharmaceutically-acceptable salt, and the compound of the Formula I obtained in the form of a salt may be converted into the free base.

Conveniently for process step (a) immediately above, a suitable activating agent is, for example, a phosphoryl halide such as phosphoryl chloride and the reaction is carried out in the presence of an organic amine base such as triethylamine or diisopropylethylamine, using a solvent or diluent such as butyronitrile or toluene, and at a temperature in the range 70 to 120° C.

Conveniently for process step (b) immediately above, the displacement reaction is conveniently carried out in the presence of a suitable inert solvent or diluent such as butyronitrile or toluene, and at a temperature in the range 70 to 120° C.

Conveniently, the intermediate of the Formula XII is not isolated as such but is used as a solution or slurry in an organic solvent. Thereby, the compound of the Formula I may be manufactured from the compound of the Formula XI in a one-pot procedure. The conversion of the compound of the Formula XI into the compound of the Formula I in this manner is illustrated hereinafter within Examples 11 and 12.

According to a further feature of the invention, there is provided a process for the manufacture of the quinazolinone of the Formula XI which comprises:—

(a) the reaction, conveniently in the presence of a suitable base as defined hereinbefore, of a quinazolinone of the Formula IV

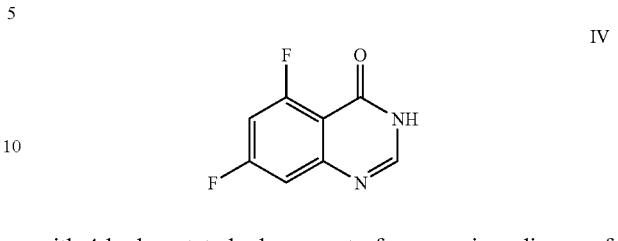

IV with 4-hydroxytetrahydropyran to form a quinazolinone of the Formula IX

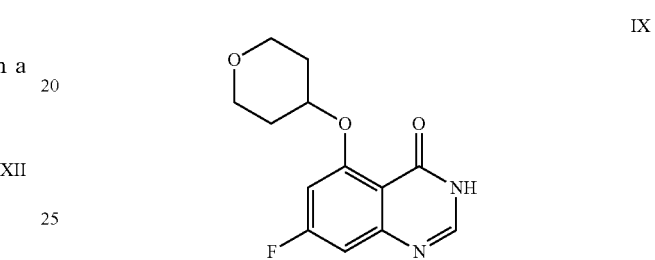

IX whereafter the compound of the Formula IX obtained in the form of the free base may be converted into a salt, and the compound of the Formula IX obtained in the form of a salt may be converted into the free base; and (b) the reaction, conveniently in the presence of a suitable base as defined hereinbefore, of the quinazolinone of the Formula IX wherein the NH functional group is protected if necessary, with 1-(2-hydroxyethyl)-4-methylpiperazine; whereafter any protecting group that is present is removed by conventional means; and whereafter the compound of the Formula XI obtained in the form of the free base may be converted into a salt; and the compound of the Formula XI obtained in the form of a salt may be converted into the free base, if necessary.

For process step (a) immediately above, the reaction may conveniently be carried out in the presence of a suitable base as defined for process step (c) above (relating to the manufacture of a quinazoline of the Formula III from a quinazoline of the Formula VI), in the presence of a suitable inert solvent or diluent or a mixture of suitable inert solvents or diluents, as defined for process step (c) above (relating to the manufacture of a quinazoline of the Formula III from a quinazoline of the Formula VI), and at a temperature in the range, for example, 0 to 250° C., conveniently in the range 25 to 125° C., more conveniently in the range 40 to 80° C.

For process step (b) immediately above, a suitable base is, for example, an alkali metal (1-6C)alkoxide, for example sodium or potassium tert-butoxide, sodium or potassium tert-pentoxide or sodium or potassium 3,7-dimethyloctoxide. The reaction is conveniently carried out in the presence of a suitable inert solvent or diluent or a mixture of suitable inert solvents or diluents, for example in an optionally substituted di-(1-6C)alkyl ether or a cyclic alkyl ether such as dibutyl ether, methyl tert-butyl ether, di-(2-methoxyethyl)ether, 1,2-dimethoxyethane, 1,2-diethoxyethane, tetrahydrofuran or 1,4-dioxan, or a dipolar aprotic solvent such as N,N-dimethylformamide, N,N-dimethylacetamide, N-methylpyrrolidin-2-one or dimethylsulphoxide. Conveniently, a suitable inert solvent or diluent with a boiling point of greater than 50° C. is employed, for example, a cyclic alkyl ether such as tetrahydrofuran or 1,4-dioxan or an optionally substituted di-(1'-6C) alkyl ether such as di-(2-methoxyethyl)ether or 1,2-diethoxyethane. Conveniently, the reaction is carried out at a temperature in the range, for example, 50 to 150° C., more conveniently at about 70° C.

The quinazolinone of the Formula XI is a novel compound that forms a further aspect of the present invention.

Crystalline Forms of AZD0530

As stated hereinbefore, the compound 4-(6-chloro-2,3-methylenedioxyanilino)-7-[2-(4-methylpiperazin-1-yl)ethoxy]-5-tetrahydropyran-4-yloxyquinazoline which is now known as AZD0530 is an inhibitor of the Src family of non-receptor tyrosine kinase enzymes and, thereby, is a selective inhibitor of the motility of tumour cells and a selective inhibitor of the dissemination and invasiveness of mammalian cancer cells leading to inhibition of metastatic tumour growth. In particular, the compound AZD0530 is an inhibitor of c-Src non-receptor tyrosine kinase and should be of value as an anti-invasive agent for use in the containment and/or treatment of solid tumour disease in the human or animal body.

The compound was disclosed as Compound No. 73 within the Table in Example 14 of International Patent Application WO 01/94341. It was stated that the compound was obtained in the form of a dihydrochloride salt and in the form of a free base. The crystallinity of the dihydrochloride salt form of AZD0530 and the free base form of AZD0530 was not mentioned.

No specific mention was made in International Patent Application WO 01/94341 that the quinazoline derivatives disclosed therein can exist in solvated as well as unsolvated forms. In particular, no particular hydrated forms of AZD0530 were disclosed.

Subsequent analysis of the free base form of AZD0530 was conducted using X-Ray Powder Diffraction analysis, Differential Scanning Calorimetry and Thermal Gravimetric analysis. It was determined that the free base form of AZD0530 was a mixture of crystalline and amorphous forms. Calorimetry showed a broad endotherm between about 30 and 85° C. There was a single broad melting endotherm with an onset at about 65° C. and with a peak at about 79° C. Gravimetric analysis showed a weight loss of about 10% of the original sample weight in the temperature range of about 25 to 120° C.

With regard to pharmaceutically-acceptable salts, it was stated in International Patent Application WO 01/94341 that a suitable pharmaceutically-acceptable salt of a compound of the Formula I therein was, for example, an acid-addition salt of a compound of the Formula I therein, for example an acid-addition salt with an inorganic or organic acid such as hydrochloric, hydrobromic, sulphuric, trifluoroacetic, citric or maleic acid; or, for example, a salt of a compound of the Formula I therein which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

It is not stated in International Patent Application WO 01/94341 that any particular compound of the Formula I therein, or any particular pharmaceutically-acceptable salt thereof, possesses a surprisingly beneficial physical form such as a crystalline physical form.

Many pharmaceutically-active compounds do not have a physical form that is suitable for isolation and handling during manufacturing and/or formulation processes. One way to overcome such deficiencies of physical form is to determine whether there is a suitable pharmaceutically-acceptable salt thereof. Another way to overcome such deficiencies of physical form is to determine whether there is a suitable pharmaceutically-acceptable polymorph. Another way to overcome such deficiencies of physical form is to form a solvate or hydrate that has a suitable form. Conveniently, such forms comprise a free-flowing, crystalline solid of reasonable melting point.

We have now found that certain forms of AZD0530, the compound of Formula I herein, including certain pharmaceutically-acceptable salts thereof are crystalline materials that possess advantageous properties. Such crystalline materials are substantially free of amorphous material.

A particular crystalline form of a compound may have physical properties that differ from those of any other crystalline or amorphous form and such properties may influence markedly the chemical and pharmaceutical processing of the compound, particularly when the compound is prepared or used on a commercial scale. For example, each crystal form of a compound may show differences in physical properties such as crystalline size and shape, melting point, density, hygroscopicity and stability. Such differences may alter the mechanical handling properties of the compound (such as the flow characteristics of the solid material) and the compression characteristics of the compound. Different crystalline forms of a compound may have different thermodynamic stabilities. In general, the more stable form, for example the more stable polymorphic form, is the more suitable physical form for formulation and processing on a commercial scale.

For example, problems could arise in the processing of a less stable form, for example a less stable polymorph. Compression forces such as those used in tabletting processes could convert some of a less stable form into a more stable form resulting in growth of crystals of the more stable form in the formulated product. This could be undesirable since any such crystallisation process could disrupt the integrity of the tablet resulting in a friable tablet of decreased tablet strength. In addition, if a variable mixture of two such forms were to be present, the dissolution rate and bioavailability of the active compound(s) could be variable as, for example, each form could have a different particle size. It is well known that particle size can affect the dissolution rate and bioavailability of a pharmaceutically-active compound. The quality of the product could therefore be affected undesirably and problems of irreproducibility of biological effect on dosing could occur.

Furthermore it is preferred that pharmaceutical compounds in the form of capsules or tablets are prepared using a stable form, for example a stable salt or the most stable polymorph, and not a metastable form or mixture of forms as there is a requirement to demonstrate to the appropriate regulatory authorities that the composition of the compound is controlled and stable. If a thermodynamically less stable form, for example a less stable polymorph, were present alone or in admixture with a thermodynamically more stable form in a tablet, it would be very difficult to control the composition of the tablet, for example the polymorphic composition of the tablet, since the quantity of the more thermodynamically stable form could tend to increase on storage.

Accordingly, these factors may have an impact on solid phase, tablet or capsule formulations of the compound and on suspension formulations thereof.

A study of the properties of the compound of AZD0530 was performed to discover whether a crystalline salt and/or a crystalline solvate or hydrate could be formed and whether polymorphism occurred. For example, the following pharmaceutically-acceptable acids were added individually to a methanolic solution of AZD0530 to establish whether any crystalline salts were formed (hydrochloric acid, citric acid, maleic acid, succinic acid, malic acid, adipic acid, malonic acid, 4-toluenesulphonic acid, methanesulphonic acid, salicylic acid, tartaric acid, ascorbic acid, fumaric acid, glycolic acid and phosphoric acid).

We have now found that surprisingly there are relatively few pharmaceutically-acceptable salts and/or solvated forms of AZD0530 that are crystalline and sufficiently stable to be of value for the pharmaceutical processing of the compound. In particular, there was initial evidence of AZD0530 crystalline salt formation only with malic acid, methanesulphonic acid, fumaric acid and phosphoric acid. Subsequent studies showed that the salts with phosphoric acid were amorphous. We have now found that salts formed with fumaric acid have preferred properties.

Samples of one or more of the particular crystalline forms of AZD0530 were analysed using a combination of X-Ray Powder Diffraction (hereinafter XRPD) analysis, Differential Scanning Calorimetry (hereinafter DSC), Thermal Gravimetric Analysis (hereinafter TGA), Diffuse Reflectance Infrared Fourier Transform (DRIFT) spectroscopy, Near Infrared (NIR) spectroscopy, solution and/or solid state nuclear magnetic resonance spectroscopy and/or water content determination by Karl Fischer analysis.

A Crystalline Difumarate Salt Form

We have found that AZD0530 and fumaric acid form a crystalline salt in the form of a difumaric acid salt which is designated hereinafter as AZD0530 difumarate. AZD0530 difumarate salt is unusual in that it possesses a crystalline physical form that is easily isolated and is also sufficiently stable that it may readily be prepared on a commercial scale at a high level of purity and in high yield.

According to this aspect of the present invention there is provided a substantially homogeneous crystalline form of 4-(6-chloro-2,3-methylenedioxyanilino)-7-[2-(4-methylpiperazin-1-yl)ethoxy]-5-tetrahydropyran-4-yloxyquinazoline, the compound of the Formula I, substantially in the form of a difumarate salt (AZD0530 difumarate).

When it is stated that the present invention relates to a substantially homogeneous crystalline form of the compound of the Formula I, the degree of crystallinity (that may be determined by XRPD means) is conveniently greater than about 60%, more conveniently greater than about 80%, preferably greater than about 90% and more preferably greater than about 95%.

When it is stated that this aspect of the present invention relates to AZD0530 difumarate, the molar ratio of each molecule of AZD0530 to each molecule of fumaric acid lies in the range from 1:1.7 to 1:2.5, conveniently in the range 1:1.8 to 1:2.3, more conveniently in the range 1:1.9 to 1:2.1, preferably having about 1 equivalent of AZD0530 to about 2 equivalents of fumaric acid.

AZD0530 difumarate is a stable form of the compound of Formula I. In particular, AZD0530 difumarate is substantially non-hygroscopic and accordingly, unlike amorphous forms of AZD0530, does not readily change form during storage if exposed to water vapour. Any such change of form can be problematic because the conversion of a less thermodynamically stable form to a more thermodynamically stable form can result in a reduction in the dissolution rate. If a variable mixture of two such forms of the compound of Formula I were to be present, the dissolution rate and bioavailability of the active compound(s) could be variable as a result of the different characteristics of the two forms.

AZD0530 difumarate exhibits other physical properties such as crystalline size and shape, melting point, density and hygroscopicity that differ when compared to other known forms of the compound of Formula I. Such differences may provide advantageous handling properties of the compound such as improved flow characteristics of the solid material and/or improved filtration during manufacture. Such advantages may provide improved formulation and processing of the compound of Formula I on a commercial scale. In particular the crystal habit of AZD0530 difumarate provides a material with advantageous filtration properties.

Moreover, AZD0530 difumarate may readily be prepared on a commercial scale at a high level of purity and in high yield.

AZD0530 difumarate has the X-ray diffraction pattern substantially as shown in FIG. 1 hereinafter which includes the peaks on the 2θ scale shown in Table 1 below (which lists the first 4 peaks and 6 of the more intense other peaks).

TABLE 1

| XRPD peaks for AZD0530 difumarate | |
|---|---|
| 2θ scale | Relative intensities |
| 5.3 | M |
| 7.1 | S |
| 9.1 | S |
| 10.6 | VS |
| 18.3 | VS |
| 19.3 | VS |
| 21.1 | VS |
| 21.4 | VS |
| 23.0 | VS |
| 24.3 | VS |

In particular, one or more of the peaks at about 7.1, 9.1 and 10.6° in Table 1 appear to be distinguishing for AZD0530 difumarate.

As mentioned hereinafter, a measurement error of peak location in an XRPD spectrum will be about plus or minus 0.3° 2θ. Such a degree of measurement error should be taken into account when it is assessed whether or not XRPD spectra have arisen from the same physical form. The person skilled in the art will understand that it is the relative position of the peaks rather than their individual peak locations that is a more reliable indicator of whether or not samples of AZD0530 difumarate are substantially the same.

As mentioned hereinafter, the intensities of the peaks in the XRPD diffractogram may also exhibit some variability, depending upon the measurement conditions used. Accordingly, in Table 1 and as quoted hereinafter, relative intensities are not stated numerically. Instead the following definitions for intensity are used:—

| % Relative Intensity* | Definition |
|---|---|
| 25-100 | VS (very strong) |
| 10-25 | S (strong) |
| 3-10 | M (medium) |
| 1-3 | W (weak) |

*The relative intensities are derived from X-ray diffraction patterns measured with variable slits.

DSC thermogram analysis of AZD0530 difumarate showed that the salt has a melting point in the range of about 231-240° C.; in other words, the onset of melting is at about 231° C. and the melting point peak is at about 237° C. Particularly, the melting point is in the range of about 233 to 239° C. More particularly, the melting point is in the range of about 234 to 238° C. More particularly, the melting point is about 237° C. Typically, DSC analysis shows that AZD0530 difumarate is a high melting solid with an onset of melting at about 235° C. and a melting point peak at about 237° C.

The DRIFT spectroscopy trace for AZD0530 difumarate is shown in FIG. 5 hereinafter which includes peaks at about 3359 (N—H), 3100-2700, 1719 (C=O), 1662, 1616, 1586, 1523, 1501, 1360-1200, 1200-1000 and 979 cm$^{-1}$. In particular, one or both of the peaks at about 3359 and 1719 cm$^{-1}$ appear to be distinguishing for AZD0530 difumarate.

An amorphous form of AZD0530 difumarate may be obtained if a sample of the material is placed in a grinder and ground for about 10 or more minutes. The amorphous nature of the ground material was shown by the absence of distinct peaks in a XRPD spectrum.

Crystalline Sesquifumarate Salt Forms

We have also found that, when AZD0530 difumarate is slurried in water, or when less than two equivalents of fumaric acid are used during AZD0530 fumaric acid salt preparation, AZD0530 fumaric acid salts are formed having a lower fumaric acid content. We have noted that such salts form a crystal lattice with sufficient space to accommodate water of crystallisation. Thereby, reasonably homogeneous crystalline salts may be obtained in the form of sesquifumaric acid salts containing between two and six equivalents of water.

In particular, a substantially homogeneous crystalline salt may be obtained in the form of a sesquifumaric acid salt tetrahydrate which is designated hereinafter as AZD0530 sesquifumarate tetrahydrate. AZD0530 sesquifumarate tetrahydrate possesses a crystalline physical form that is isolable and of reasonable stability.

The degree of crystallinity (that may be determined by XRPD means) of this substantially homogeneous crystalline form is conveniently greater than about 60%, more conveniently greater than about 80%, preferably greater than about 90%. Most preferably, the degree of crystallinity is greater than about 95%.

In AZD0530 sesquifumarate tetrahydrate, the molar ratio of each molecule of AZD0530 to each molecule of fumaric acid lies in the range from 1:1.3 to 1:1.7, conveniently in the range 1:1.4 to 1:1.6, more conveniently having about 1 equivalent of AZD0530 to about 1.5 equivalents of fumaric acid.

In AZD0530 sesquifumarate tetrahydrate, the molar ratio of each molecule of AZD0530 to each molecule of water lies in the range from 1:3.5 to 1:4.5, conveniently in the range 1:3.7 to 1:4.3, more conveniently having about 1 equivalent of AZD0530 to about 4 equivalents of water.

AZD0530 sesquifumarate tetrahydrate has the X-ray diffraction pattern substantially as shown in FIG. 2 which includes peaks on the 2θ scale as shown in Table 2 below (which lists 10 of the most intense XRPD peaks).

TABLE 2

XRPD peaks for AZD0530 sequifomarate tetrahydrate

| 2θ scale | Relative intensities |
|---|---|
| 2.8 | VS |
| 10.3 | VS |
| 16.4 | S |
| 18.9 | S |
| 19.2 | VS |
| 20.1 | S |
| 21.1 | S |
| 22.6 | VS |
| 23.3 | VS |
| 24.1 | S |

In particular, one or more of the peaks at about 2.8, 10.3 and 22.6° in Table 2 appear to be unique to AZD0530 sesquifumarate tetrahydrate.

DSC thermogram analysis for AZD0530 sesquifumarate tetrahydrate showed that the salt has an initial thermal event between about 25 and 100° C. which is believed to be due to the loss of the water of hydration. An exotherm occurs above about 150° C. corresponding to crystallisation of AZD0530 difumarate. On subsequent heating, a further thermal event occurs between about 230 and 240° C. corresponding to the melting point of AZD0530 difumarate.

The TGA for AZD0530 sesquifumarate tetrahydrate showed a weight loss of between about 8% and 10% between about 30 and 130° C. corresponding to the loss of about four equivalents of water.

The DRIFT spectroscopy trace for AZD0530 sesquifumarate tetrahydrate is shown in FIG. 6 hereinafter which includes peaks at about 3345 (N—H), 3100-2700, 1698 (C=O), 1660-1450 and 1400-1000 cm$^{-1}$. In particular, one or both of the peaks at about 3345 and 1698 cm$^{-1}$ appear to be distinguishing for AZD0530 sesquifumarate tetrahydrate.

A Crystalline Trihydrate Free Base Form

We have also found that AZD0530 may be crystallised from organic solvents that are wet in the form of a crystalline trihydrate which is designated hereinafter as AZD0530 trihydrate. AZD0530 trihydrate is unusual in that it possesses a crystalline physical form that is easily isolated and is also sufficiently stable that it may readily be prepared on a commercial scale at a high level of purity and in high yield.

According to this aspect of the present invention there is provided a substantially homogeneous crystalline form of 4-(6-chloro-2,3-methylenedioxyanilino)-7-[2-(4-methylpiperazin-1-yl)ethoxy]-5-tetrahydropyran-4-yloxyquinazoline, the compound of the Formula I, substantially in the form of a trihydrate (AZD0530 trihydrate).

When it is stated that the present invention relates to a substantially homogeneous crystalline trihydrate form of the compound of the Formula I, the degree of crystallinity (that may be determined by XRPD means) is conveniently greater than about 90%, and more conveniently greater than about 95%.

When it is stated that this aspect of the present invention relates to AZD0530 trihydrate, the molar ratio of each molecule of AZD0530 to each molecule of water lies in the range from 1:2 to 1:4, conveniently in the range 1:2.5 to 1:3.5, more conveniently in the range 1:2.75 to 1:3.25, preferably having about 1 equivalent of AZD0530 to about 3 equivalents of water.

AZD0530 trihydrate is a stable form of the compound of Formula I. In particular, AZD0530 trihydrate is stable in the presence of water. For example, when AZD0530 is prepared as an aqueous suspension the resulting suspension is stable, whereas aqueous suspensions prepared using other forms of the compound of Formula I may tend to convert partially or completely to hydrated forms of AZD0530.

AZD0530 trihydrate may readily be prepared on a commercial scale at a high level of purity and in high yield. In addition AZD0530 trihydrate can be converted into a crystalline anhydrous form of AZD0530 and into certain crystalline pharmaceutically-acceptable salt forms of AZD0530. The preparation of AZD0530 trihydrate, purification thereof and conversion to other crystalline forms is beneficial in terms of yield and purity.

AZD0530 trihydrate has the X-ray diffraction pattern substantially as shown in FIG. 3 hereinafter which includes the peaks on the 2 theta (θ) scale shown in Table 3 below (which lists 10 of the most intense XRPD peaks).

TABLE 3

XRPD peaks for AZD0530 trihydrate

| 2θ scale | Relative intensities |
|---|---|
| 7.4 | VS |
| 13.8 | M |
| 14.8 | M |
| 16.0 | M |
| 17.8 | M |
| 19.7 | M |
| 20.2 | M |
| 21.3 | M |
| 22.3 | M |
| 24.0 | M |

In particular, the peak at about 13.8° and, especially, the peak at about 16.0° in Table 3 appear to be distinguishing for AZD0530 trihydrate compared to the crystalline anhydrous form (see below).

As mentioned hereinafter, a measurement error of peak location in an XRPD spectrum will be about plus or minus 0.3° 2θ. Such a degree of measurement error should be taken into account when it is assessed whether or not XRPD spectra have arisen from the same physical form. The person skilled in the art will understand that it is the relative position of the peaks rather than their individual peak locations that is a more reliable indicator of whether or not samples of AZD0530 trihydrate are substantially the same.

DSC thermogram analysis of AZD0530 trihydrate showed a broad endotherm between about 50 and 94° C. which is believed to be due to the loss of the water. The endotherm showed an onset at about 65° C. with a peak at about 75° C.

The TGA for AZD0530 trihydrate showed a weight loss of about 9% between about 30 and 110° C. corresponding to the loss of about three equivalents of water.

A Crystalline Anhydrous Free Base Form

We have also found that AZD0530 can be obtained in two anhydrous forms, namely an amorphous, non-crystalline form that does not have a defined melting point and a highly crystalline form that has a narrow, well defined melting point. We have found that AZD0530 trihydrate can be readily converted to a substantially homogeneous crystalline anhydrous form, hereinafter anhydrous AZD0530. Accordingly, crystallisation of AZD0530 trihydrate and subsequent conversion to anhydrous AZD0530 provides a means for preparing anhydrous AZD0530 in high purity. Anhydrous AZD0530 is unusual in that it possesses a crystalline physical form that is easily isolated and is also sufficiently stable under substantially anhydrous conditions that it may readily be prepared on a commercial scale at a high level of purity and in high yield.

The degree of crystallinity (that may be determined by XRPD means) of this substantially homogeneous crystalline form is conveniently greater than about 60%, more conveniently greater than about 80%, preferably greater than about 90% and more preferably greater than about 95%.

Anhydrous AZD0530 is a stable form of the compound of Formula I. In particular, anhydrous AZD0530 is very stable in the absence of water. However, anhydrous AZD0530 is prone to convert to AZD0530 trihydrate during storage if substantially anhydrous storage conditions are not maintained.

Anhydrous AZD0530 may readily be prepared on a commercial scale at a high level of purity and in high yield. In addition, anhydrous AZD0530 can be converted into certain crystalline pharmaceutically-acceptable salt forms of AZD0530.

Anhydrous AZD0530 has the X-ray diffraction pattern substantially as shown in FIG. 4 hereinafter which includes peaks on the 2θ scale shown in Table 4 below (which lists 10 of the most intense XRPD peaks).

TABLE 4

XRPD peaks for anhydrous AZD0530

| 2θ scale | Relative intensities |
|---|---|
| 7.5 | VS |
| 15.1 | S |
| 17.0 | S |
| 18.0 | S |
| 19.3 | M |
| 20.2 | VS |
| 20.4 | VS |
| 22.3 | S |
| 23.3 | VS |
| 27.7 | M |

One or more of the strong peaks at about 15.1, 17.0 and 18.0° and, in particular, one or both of the very strong peaks at about 20.4 and 23.3° in Table 4 appear to be distinguishing for anhydrous AZD0530 compared to the trihydrate form (see above).

As mentioned hereinafter, a measurement error of peak location in an XRPD spectrum will be about plus or minus 0.3° 2θ. Such a degree of measurement error should be taken into account when it is assessed whether or not XRPD spectra have arisen from the same physical form. The person skilled in the art will understand that it is the relative position of the peaks rather than their individual peak locations that is a more reliable indicator of whether or not samples of anhydrous AZD0530 are substantially the same.

DSC thermogram analysis of anhydrous AZD0530 showed a thermal event between about 133 and 152° C. The onset of melting was at about 142° C. with a melting point peak at about 144° C.

The following particular crystalline forms of the compound of the Formula I are disclosed herein:—
  (i) AZD0530 difumarate;
  (ii) AZD0530 sesquifumarate tetrahydrate;
  (iii) AZD0530 trihydrate; and
  (iv) anhydrous AZD0530.

Each of these entities possesses the same pharmacological properties as those disclosed in International Patent Application WO 01/94341 for compounds such as 4-(6-chloro-2,3-methylenedioxyanilino)-7-[2-(4-methylpiperazin-1-yl)ethoxy]-5-tetrahydropyran-4-yloxyquinazoline (AZD0530). In particular, each of these entities is an inhibitor of non-receptor tyrosine kinases such as c-Src which provides selective inhibition of the motility of tumour cells and selective inhibition of the dissemination and invasiveness of mammalian cancer cells leading to inhibition of metastatic tumour growth. In particular, each of these entities should be of value as an anti-invasive agent for use in the containment and/or treatment of solid tumour disease. These crystalline forms of the compound of the Formula I are described collectively hereinafter as 'the active substance of the invention'.

In order to use the active substance of the invention for the treatment of mammals including humans, it is normally formulated in accordance with standard pharmaceutical practice as a pharmaceutical composition.

According to another aspect of the invention there is provided a pharmaceutical composition which comprises the active substance of the invention in association with a pharmaceutically-acceptable diluent or carrier.

For example, the compositions of the invention may be in a form adapted for oral administration (for example as tablets, lozenges, hard or soft capsules, aqueous or oily suspensions, emulsions, dispersible powders or granules, syrups or elixirs), for topical administration (for example as creams, ointments, gels, or aqueous or oily solutions or suspensions), for insufflation (for example as an aqueous suspension) or for parenteral administration (for example as a sterile aqueous or oily solution for intravenous, subcutaneous, intraperitoneal or intramuscular dosing or as a suppository for rectal dosing).

A preferred method of administration is oral administration. The active substance of the invention is conveniently administered orally in the form of tablets.

The compositions of the invention may be obtained by conventional procedures using conventional pharmaceutical excipients that are well known in the art. Thus, compositions intended for oral use may contain, for example, one or more colouring, sweetening, flavouring and/or preservative agents. For example, the composition may contain one or more fillers, binders, disintegrants and/or lubricants. Suitable fillers include, for example, lactose, sugar, starches, modified starches, mannitol, sorbitol, inorganic salts, cellulose derivatives (for example microcrystalline cellulose, cellulose), calcium sulphate, xylitol and lactitol. Suitable binders include, for example, polyvinylpyrrolidone, lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatin and sodium alginate. Suitable disintegrants include, for example, croscarmellose sodium, crospovidone, polyvinylpyrrolidone, sodium starch glycollate, corn starch, microcrystalline cellulose, hydroxypropyl methylcellulose and hydroxypropyl cellulose. Suitable lubricants include, for example, magnesium stearate, stearic acid, palmitic acid, calcium stearate, talc, carnuba wax, hydrogenated vegetable oils, mineral oil, polyethylene glycols and sodium stearyl fumarate. Additional conventional excipients which may be added include preservatives, stabilisers, antioxidants, silica flow conditioners, antiadherents or glidants. Other suitable fillers, binders, disintegrants, lubricants and additional excipients which may be used are described in the following reference works: Handbook of Pharmaceutical Excipients, 3rd Edition; The Theory and Practice of Industrial Pharmacy, 3rd Edition 1986; Pharmaceutical Dosage Forms 1998; Modern Pharmaceutics, 3rd Edition 1995; and Remington's Pharmaceutical Sciences, 20th Edition 2000.

The amount of the active substance of the invention that is combined with one or more excipients to produce a single dosage form will necessarily vary depending upon the host treatment and the particular route of administration. For example, a formulation intended for oral administration to humans will conveniently contain, for example, from 0.5 mg to 0.5 g of active agent (conveniently from 1 to 250 mg, more conveniently from 10 to 200 mg or from 25 to 100 mg) compounded with an appropriate and convenient amount of excipient which may vary from about 5 to about 98 percent by weight of the total composition. Preferably, the formulation will comprise, for example, from 50 mg to 500 mg of active substance. More preferably, the formulation will comprise, for example, from 100 mg to 250 mg of active substance, especially from 125 mg to 225 mg of active substance.

In using the active substance of the invention for therapeutic or prophylactic purposes it will generally be administered so that a daily oral dose in the range, for example, 0.1 mg/kg to 20 mg/kg body weight is received, given if required in divided doses. Preferably, a daily oral dose in the range, for example, 1 mg/kg to 10 mg/kg body weight is received. More preferably, a daily dose in the range, for example, 2 mg/kg to 8 mg/kg body weight is received.

The active substance of the invention shows an acceptable toxicity profile.

The active substance of the invention possesses the same pharmacological properties as those disclosed in International Patent Application WO 01/94341 for the compound of the Formula I therein. In particular, the active substance of the invention is an inhibitor of non-receptor tyrosine kinases such as c-Src which provides selective inhibition of the motility of tumour cells and selective inhibition of the dissemination and invasiveness of mammalian cancer cells leading to inhibition of metastatic tumour growth. In particular, the active substance of the invention should be of value as an anti-invasive agent for use in the containment and/or treatment of solid tumour disease. For example, the active substance of the invention is useful for the treatment of many common human cancers such as lung (including small cell lung cancer and non small cell lung cancer), breast, prostate, ovarian, colorectal, gastric, brain (including glioma and pituitary adenoma), head and neck, bladder, pancreas, oesophageal, stomach, renal, skin (including malignant melanoma), gynaecological (including cervical, endometrial, vaginal, vulval and uterine) and thyroid cancer and in the treatment of a range of leukaemias and lymphoid malignancies such as CML and ALL and in the treatment of solid tumours such as carcinomas and sarcomas.

The pharmacological properties of the active substance of the invention may be assessed using, for example, one or more of the test procedures disclosed in International Patent Application WO 01/94341 or equivalent test procedures that are well within the compass of the man skilled in the art. Such test procedures from that patent application are incorporated herein by reference.

According to a further aspect of the present invention there is provided the active substance of the invention as defined hereinbefore for use in a method of treatment of the human or animal body by therapy.

As stated above, it is known that the predominant role of c-Src non-receptor tyrosine kinase is to regulate cell motility which is necessarily required for a localised tumour to progress through the stages of dissemination into the blood stream, invasion of other tissues and initiation of metastatic tumour growth. We have found that the active substance of the invention possesses potent anti-tumour activity which it is believed is obtained by way of inhibition of one or more of the non-receptor tyrosine-specific protein kinases such as c-Src kinase that are involved in the signal transduction steps which lead to the invasiveness and migratory ability of metastasising tumour cells.

Accordingly, the active substance of the invention is of value as an anti-tumour agent, in particular as a selective inhibitor of the motility, dissemination and invasiveness of mammalian cancer cells leading to inhibition of metastatic tumour growth. Particularly, the active substance of the invention is of value as an anti-invasive agent in the containment and/or treatment of solid tumour disease. Particularly, the active substance of the invention is expected to be useful in the prevention or treatment of those tumours which are sensitive to inhibition of one or more of the multiple non-receptor tyrosine kinases such as c-Src kinase that are involved in the signal transduction steps which lead to the invasiveness and migratory ability of metastasising tumour cells. Further, the active substance of the invention is expected to be useful in the prevention or treatment of those tumours which are mediated alone or in part by inhibition of the enzyme c-Src, i.e. the active substance of the invention may be used to produce a c-Src enzyme inhibitory effect in a warm-blooded animal in need of such treatment. Specifically, the active substance of the invention is expected to be useful in the prevention or treatment of solid tumour disease.

Thus, according to this aspect of the invention, there is provided the use of the active substance of the invention as defined hereinbefore in the manufacture of a medicament for use as an anti-invasive agent in the containment and/or treatment of solid tumour disease.

According to a further feature of this aspect of the invention, there is provided a method for producing an anti-invasive effect by the containment and/or treatment of solid tumour disease in a warm-blooded animal, such as man, in need of such treatment which comprises administering to said animal an effective amount of the active substance of the invention as defined hereinbefore.

According to a further aspect of the invention, there is provided the use of the active substance of the invention as defined hereinbefore in the manufacture of a medicament for use in the prevention or treatment of solid tumour disease in a warm-blooded animal such as man.

According to a further feature of this aspect of the invention, there is provided a method for the prevention or treatment of solid tumour disease in a warm-blooded animal, such as man, in need of such treatment which comprises administering to said animal an effective amount of the active substance of the invention as defined hereinbefore.

According to a further aspect of the invention, there is provided the use of the active substance of the invention as defined hereinbefore in the manufacture of a medicament for use in the prevention or treatment of those tumours which are sensitive to inhibition of non-receptor tyrosine kinases such as c-Src kinase that are involved in the signal transduction steps which lead to the invasiveness and migratory ability of metastasising tumour cells.

According to a further feature of this aspect of the invention, there is provided a method for the prevention or treatment of those tumours which are sensitive to inhibition of non-receptor tyrosine kinases such as c-Src kinase that are involved in the signal transduction steps which lead to the invasiveness and migratory ability of metastasising tumour cells which comprises administering to said animal an effective amount of the active substance of the invention as defined hereinbefore.

According to a further aspect of the invention, there is provided the use of the active substance of the invention as defined hereinbefore in the manufacture of a medicament for use in providing a c-Src kinase inhibitory effect.

According to a further feature of this aspect of the invention, there is provided a method for providing a c-Src kinase inhibitory effect which comprises administering to said animal an effective amount of the active substance of the invention as defined hereinbefore.

The anti-cancer treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:—

(i) other anti-invasion agents (for example other c-Src kinase family inhibitors like N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), metalloproteinase inhibitors like marimastat and inhibitors of urokinase plasminogen activator receptor function);

(ii) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agents within their approved dosage ranges.

According to this aspect of the invention there is provided a pharmaceutical product comprising the active substance of the invention as defined hereinbefore and an additional anti-cancer agent as defined hereinbefore for the conjoint treatment of cancer.

Processes for the preparation of the following particular crystalline forms of the compound of the Formula I are disclosed herein, namely processes:—

(i) for preparing AZD0530 difumarate;
(ii) for preparing AZD0530 sesquifumarate tetrahydrate;
(iii) for preparing AZD0530 trihydrate; and
(iv) for preparing anhydrous AZD0530.

According to a further aspect of the present invention, there is provided a process for preparing a compound of the Formula I substantially in the form of AZD0530 difumarate which comprises:—

(a) contacting 4-(6-chloro-2,3-methylenedioxyanilino)-7-[2-(4-methylpiperazin-1-yl)ethoxy]-5-tetrahydropyran-4-yloxyquinazoline with fumaric acid for a sufficient time to form AZD0530 difumarate; and (b) isolating the AZD0530 difumarate.

The 4-(6-chloro-2,3-methylenedioxyanilino)-7-[2-(4-methylpiperazin-1-yl)ethoxy]-5-tetrahydropyran-4-yloxyquinazoline used as the starting material in process step (a) immediately above may be any form of the compound of Formula I, for example when prepared as described in the prior art or when prepared as one of the forms described herein such as AD0530 trihydrate.

Conveniently, conversion to AZD0530 difumarate is effected by preparing a solution of the 4-(6-chloro-2,3-methylenedioxyanilino)-7-[2-(4-methylpiperazin-1-yl)ethoxy]-5-tetrahydropyran-4-yloxyquinazoline starting material in one or more suitable solvents and by adding fumaric acid. Conveniently, a molar excess of fumaric acid may be used to ensure substantially complete conversion of the 4-(6-chloro-2,3-methylenedioxyanilino)-7-[2-(4-methylpiperazin-1-yl) ethoxy]-5-tetrahydropyran-4-yloxyquinazoline starting material to the AZD0530 difumarate (i.e. the molar ratio of fumaric acid to quinazoline compound is at least 2:1). The upper limit of the fumaric acid concentration is not critical. Conveniently, a slight molar excess of fumaric acid is used. For example, the molar ratio of fumaric acid to the quinazoline compound is suitably from about 2:1 to 10:1, particularly from about 2:1 to 3:1, more particularly about 2.2:1.

In a particular embodiment, a solution of the 4-(6-chloro-2,3-methylenedioxyanilino)-7-[2-(4-methylpiperazin-1-yl) ethoxy]-5-tetrahydropyran-4-yloxyquinazoline starting material is prepared in a mixture of one or more organic solvents, optionally containing water as a co-solvent. Suitable organic solvents are water-miscible polar organic solvents, such as polar protic solvents, for example (1-4C)alcohols, particularly methanol, ethanol, isopropanol and n-butanol, polar non-protic solvents such as aliphatic esters, for example a (1-4C)alkyl (2-3C)alkanoate ester, particularly ethyl acetate, aliphatic (3-6C)ketones, particularly acetone and methyl ethyl ketone, aliphatic amides, particularly N,N-dimethylformamide, and nitrites, particularly acetonitrile. Conveniently, a non-water miscible co-solvent may be added to the water miscible solvent. Suitable such co-solvents include, for example, aromatic solvents such as toluene. Particular convenient organic solvents include, for example, isopropanol or ethyl acetate, or a mixture thereof.

For the quinazoline compound, the specific amount of organic solvent used will be dependent upon the organic solvent selected and the conditions under which the quinazoline compound is contacted with the fumaric acid. In the case of solvents such as isopropanol or ethyl acetate a range of 0.1 to 30 ml/g, such as 2 to 20 ml/g and particularly approximately 10 ml/g is suitable for the quinazoline compound, wherein "ml/g" refers to the volume of organic solvent per g of the 4-(6-chloro-2,3-methylenedioxyanilino)-7-[2-(4-methylpiperazin-1-yl)ethoxy]-5-tetrahydropyran-4-yloxyquinazoline. A single organic solvent may be used or two or more organic solvents, for example a mixture of ethyl acetate and isopropanol (suitably in a volume ratio of approximately 1:1), may be used. Water may be added as a co-solvent. Conveniently, a suitable ratio by volume of organic solvent (such as isopropanol) to water lies within the range 50:1 to 2:1, particularly within the range 10:1 to 5:1.

For the fumaric acid, the specific amount of solvent used will be dependent upon the organic solvent selected, whether or not water is used as a co-solvent and the conditions under which the fumaric acid is contacted with the quinazoline compound. In the case of solvents such as isopropanol or ethyl acetate a range of 0.1 to 60 ml/g, such as 2 to 30 ml/g and particularly approximately 15 ml/g is suitable for the fumaric acid. A single organic solvent may be used or two or more organic solvents, for example a mixture of ethyl acetate and isopropanol (suitably in a volume ratio of approximately 1:1), may be used. Water may be added as a co-solvent. Conveniently, a suitable ratio by volume of organic solvent (such as isopropanol) to water lies within the range 50:1 to 3:1, particularly within the range 15:1 to 5:1, more particularly about 10:1.

Optionally, one or more seed crystals of AZD0530 difumarate may be added to enhance initiation of the conversion and/or the rate of conversion to AZD0530 difumarate.

The time required for conversion to the AZD0530 difumarate is dependent upon the particular reaction conditions used, such as temperature, presence of an organic solvent and whether seeding crystals are used. Generally, a reaction time of, for example, from 5 minutes to 48 hours is suitable.

Alternatively, the amount of organic solvent may be insufficient to completely dissolve the 4-(6-chloro-2,3-methylenedioxyanilino)-7-[2-(4-methylpiperazin-1-yl)ethoxy]-5-tetrahydropyran-4-yloxyquinazoline starting material such that a slurry is retained throughout the process. Conveniently, by retaining the compound of the Formula I in a slurry during the process, the AZD0530 difumarate can be formed without the need to induce crystallisation by, for example, cooling the mixture or evaporating solvent. Accordingly the slurry process may be operated at a substantially constant temperature. Without wishing to be bound by theory, it is thought that the process proceeds via a mechanism of localised dissolution of the 4-(6-chloro-2,3-methylenedioxyanilino)-7-[2-(4-methylpiperazin-1-yl)ethoxy]-5-tetrahydropyran-4-yloxyquinazoline starting material and subsequent crystallisation of AZD0530 difumarate. Hence the slurry conversion process described herein is thought to be a portionwise dissolution and conversion of the starting material to AZD0530 difumarate.

According to this aspect of the present invention, there is also provided a process for preparing a compound of the Formula I substantially in the form of AZD0530 difumarate which comprises the steps:—

(a) dissolving the compound 4-(6-chloro-2,3-methylenedioxyanilino)-7-[2-(4-methylpiperazin-1-yl)ethoxy]-5-tetrahydropyran-4-yloxyquinazoline in a solvent system comprising an organic solvent and water;

(b) adding a solution of fumaric acid in a solvent system comprising an organic solvent and water;

(c) reducing the temperature of the solvent system to induce nucleation;

(d) maintaining the mixture at a temperature below that at which nucleation has commenced; and (e) isolating the crystalline AZD0530 difumarate.

This crystallisation process for preparing the AZD0530 difumarate enables the difumarate salt to be prepared in high purity.

Suitable organic solvents in the solvent system include organic solvents which are water-soluble at the temperature at which the starting material in process step (a) immediately above is dissolved. Suitable organic solvents include, for example, weakly polar organic solvents such as aliphatic di-(1-6C)alkyl ethers or (4-7C)cyclic ethers such as tetrahydrofuran, more polar protic solvents, for example (2-6C)alcohols such as ethanol and isopropanol, polar non-protic solvents such as (1-4C)alkyl (2-3C)alkanoate esters such as ethyl acetate, aliphatic (3-6C)ketones such as acetone, aliphatic amides such as N,N-dimethylformamide or N-methylpyrrolidin-2-one and nitriles such as acetonitrile. A particular organic solvent is, for example ethyl acetate. A single organic solvent or a mixture of one or more of the above solvents may be used.

Conveniently, a molar excess of fumaric acid may be used to ensure substantially complete conversion of the 4-(6-chloro-2,3-methylenedioxyanilino)-7-[2-(4-methylpiperazin-1-yl)ethoxy]-5-tetrahydropyran-4-yloxyquinazoline starting material to the AZD0530 difumarate (i.e. the molar ratio of fumaric acid to quinazoline compound is at least 2:1). The upper limit of the fumaric acid concentration is not critical. Conveniently, a slight molar excess of fumaric acid is used. For example, the molar ratio of fumaric acid to the quinazoline compound is suitably from about 2:1 to 10:1, particularly from about 2:1 to 3:1, more particularly about 2.2:1.

For the quinazoline compound, the specific amount of organic solvent used will be dependent upon the organic solvent selected and the conditions under which the quinazoline compound is contacted with the fumaric acid. In the case of solvents such as isopropanol or ethyl acetate a range of 0.1 to 30 ml/g, such as 2 to 20 ml/g and particularly approximately 10 ml/g is suitable. A single organic solvent may be used or two or more organic solvents, for example a mixture of ethyl acetate and isopropanol (suitably in a volume ratio of approximately 1:1), may be used. Water is conveniently added as a co-solvent. Conveniently, a suitable ratio by volume of organic solvent (such as isopropanol) to water lies within the range 50:1 to 2:1, particularly within the range 10:1 to 5:1.

For the fumaric acid, the specific amount of solvent used will be dependent upon the organic solvent selected, whether or not water is used as a co-solvent and the conditions under which the fumaric acid is contacted with the quinazoline compound. In the case of solvents such as isopropanol or ethyl acetate a range of 0.1 to 60 ml/g, such as 2 to 30 ml/g and particularly approximately 15 ml/g is suitable. A single organic solvent may be used or two or more organic solvents, for example a mixture of ethyl acetate and isopropanol (suitably in a volume ratio of approximately 1:1), may be used. Water is conveniently added as a co-solvent. Conveniently, a suitable ratio by volume of organic solvent (such as isopropanol) to water lies within the range 50:1 to 3:1, particularly within the range 15:1 to 5:1, more particularly about 10:1.

The compound 4-(6-chloro-2,3-methylenedioxyanilino)-7-[2-(4-methylpiperazin-1-yl)ethoxy]-5-tetrahydropyran-4-yloxyquinazoline may be dissolved in step (a) of the process by heating the compound in the solvent system until substantially all of the compound, has dissolved. Likewise, the fumaric acid may be dissolved in step (b) of the process by heating the compound in the solvent system until substantially all of the compound has dissolved. Conveniently, each compound is heated to about the reflux temperature of the solvent systems for sufficient time to complete dissolution. More conveniently, each compound is heated to a temperature in the range of about 30 to 100° C., preferably in the range 35 to 80° C., to complete dissolution. If necessary, either or both warmed solutions may be filtered to remove insoluble material. Whilst maintaining the temperature of the solution of the quinazoline compound in the range of about 50 to 100° C., conveniently in the range of about 60 to 90° C., the warm fumaric acid solution is added. The mixture may then be allowed to cool slightly, for example to a temperature in the range of about 50 to 80° C. to encourage nucleation of the AZD0530 difumarate. It will be appreciated that the nucleation may occur either spontaneously or on adding one or more seed crystals. Conveniently, the mixture is maintained at a temperature of about 75° C., seed crystals are added to encourage nucleation of the AZD0530 difumarate and the mixture is maintained at a temperature of about 75° C. for several hours to allow the crystallisation process to continue. The mixture may then be allowed to cool at a controlled rate to ambient temperature. A suitable cooling rate is, for example, about 20° C. per hour. The crystalline AZD0530 difumarate so obtained may be isolated by any conventional method, for example by filtration or centrifugation.

When one or more seed crystals are used to initiate nucleation in the crystallisation process described above, the seed crystals are preferably crystals of the AZD0530 difumarate which may be prepared using any suitable method, for example using the method described within the accompanying Examples.

It will be appreciated by the man skilled in the art that the procedures described above may be varied using routine skill and knowledge. For example, an inverse addition procedure may be used whereby the solution of AZD0530 is added to the solution of fumaric acid. Further, for example, provided that AZD0530 difumarate is obtained substantially free of any other AZD0530 form, any of the quantities of the compound 4-(6-chloro-2,3-methylenedioxyanilino)-7-[2-(4-methylpiperazin-1-yl)ethoxy]-5-tetrahydropyran-4-yloxyquinazoline and fumaric acid that are reacted, the nature and volume of the solvent and any co-solvent, the ratio of the component solvents if a solvent mixture is employed, the volume of water used and the temperatures of the dissolution and crystallisation phases may be varied. For example, nucleation of the difumarate may be induced by, for example, the evaporation of some of the solvent. Alternatively, nucleation could be induced by the addition of a suitable antisolvent for the difumarate compound, thereby creating supersaturation of the solution from which AZD0530 difumarate crystallises.

There is also provided a process for preparing a compound of the Formula I substantially in the form of AZD0530 sesquifumarate tetrahydrate which comprises the steps:—

(a) dissolving AZD0530 difumarate in water or a solvent system comprising an organic solvent and water;

(b) causing partial evaporation of the solvent system to induce nucleation;

(c) cooling the mixture to a temperature below ambient temperature; and (d) isolating the crystalline AZD0530 sesquifumarate tetrahydrate.

This crystallisation process for preparing the AZD0530 sesquifumarate tetrahydrate enables the sesquifumarate tetrahydrate salt to be prepared in high purity.

Suitable organic solvents in the solvent system include organic solvents which are water-soluble at the temperature at which the starting material in process step (a) immediately above is dissolved. Suitable organic solvents include, for example, nitrites such as acetonitrile and polar protic solvents, for example (2-6C)alcohols such as methanol, ethanol and isopropanol. A particular organic solvent for use in admixture with water is, for example acetonitrile. A single organic solvent or a mixture of one or more of the above solvents may be used. Conveniently, a non-water miscible co-solvent may be added to the water miscible solvent. Suitable such co-solvents include, for example, aromatic solvents such as toluene. More conveniently, water is used as the solvent.

Evaporation of the solvent can be effected at ambient temperature by, for example, allowing the solution to stand in an open vessel. Alternatively, the evaporation step may be carried out at a higher temperature, for example at a temperature in the range of about 40 to 80° C., conveniently at about 60° C. Conveniently, a flow of gas such as air or nitrogen may be passed into or across the surface of the solution to speed up solvent evaporation. Once nucleation has commenced, the crystallisation mixture is conveniently cooled to a temperature below ambient temperature to allow crystallisation to continue. Conveniently, the mixture is cooled to a temperature below about 10° C., more conveniently to a temperature of about 5° C.

It will be appreciated by the man skilled in the art that the procedures described above may be varied using routine skill and knowledge. For example, provided that AZD0530 sesquifumarate tetrahydrate is obtained substantially free of any other AZD0530 form, any of the quantities of the AZD0530 difumarate, the volume of water used, the nature and volume of any co-solvent employed, and the temperatures of the dissolution, evaporation and cooling phases may be varied. For example, nucleation could be induced by the addition of a suitable antisolvent, thereby creating supersaturation of the solution from which AZD0530 sesquifumarate tetrahydrate crystallises.

According to a further aspect of the present invention, there is provided a process for preparing a compound of the Formula I substantially in the form of AZD0530 trihydrate which comprises the steps:—

(a) dissolving the compound 4-(6-chloro-2,3-methylenedioxyanilino)-7-[2-(4-methylpiperazin-1-yl)ethoxy]-5-tetrahydropyran-4-yloxyquinazoline in a solvent system comprising water and an organic solvent;

(b) reducing the temperature of the solvent system to induce nucleation;

(c) maintaining the mixture at a temperature below that at which nucleation has commenced; and (d) isolating the crystalline AZD0530 trihydrate.

Suitable organic solvents in the solvent system include organic solvents which are water-soluble at the temperature at which the starting material in step (a) of the process is dissolved. Suitable organic solvents include, for example, weakly polar organic solvents such as aliphatic di-(1-6C)allyl ethers or (4-7C)cyclic ethers such as tetrahydrofuran, more polar protic solvents, for example (2-6C)alcohols such as ethanol and isopropanol, polar non-protic solvents such as (1-4C)alkyl (2-3C)alkanoate esters such as ethyl acetate, aliphatic (3-6C)ketones such as acetone, aliphatic amides such as N,N-dimethylformamide or N-methylpyrrolidin-2-one and nitriles such as acetonitrile. A particular organic solvent is, for example ethyl acetate. A single organic solvent or a mixture of one or more of the above solvents may be used.

Generally a molar excess of water is used in the solvent system (i.e. the molar ratio of water:4-(6-chloro-2,3-methylenedioxyanilino)-7-[2-(4-methylpiperazin-1-yl)ethoxy]-5-tetrahydropyran-4-yloxyquinazoline is at least 3:1). The upper limit of water concentration is not critical, however, generally a large molar excess of water is used. For example the molar ratio of water to 4-(6-chloro-2,3-methylenedioxyanilino)-7-[2-(4-methylpiperazin-1-yl)ethoxy]-5-tetrahydropyran-4-yloxyquinazoline is suitably from about 3:1 to 1000:1 or more, particularly from about 3:1 to about 400:1.

Optionally, a co-solvent may be used in the solvent system. Suitable co-solvents include, for example, aromatic hydrocarbons such as toluene and aliphatic halogenated hydrocarbons such as halogeno-(1-6C)alkanes, for example 1,2-dichloroethane.

The compound 4-(6-chloro-2,3-methylenedioxyanilino)-7-[2-(4-methylpiperazin-1-yl)ethoxy]-5-tetrahydropyran-4-yloxyquinazoline may be dissolved in step (a) of the process by heating the compound in the solvent system until substantially all of the compound has dissolved. Conveniently, the compound in the solvent system in step (a) of the process is heated to about the reflux temperature of the solvent system for sufficient time to completely dissolve the compound. The solution of the compound 4-(6-chloro-2,3-methylenedioxyanilino)-7-[2-(4-methylpiperazin-1-yl)ethoxy]-5-tetrahydropyran-4-yloxyquinazoline may then be removed from the heat source and allowed to cool to a temperature in the range of 25 to 60° C. to encourage nucleation of the AZD0530 trihydrate or it may be cooled further, for example to ambient temperature. Conveniently, the solution may be removed from the heat source and allowed to cool to about 50° C. to encourage nucleation of the AZD0530 trihydrate. The mixture may be reheated to about 55° C. and then be allowed to cool at a controlled rate to about 50° C. A suitable cooling rate is, for example, about 10° C. per hour. It will be appreciated that the nucleation may occur either spontaneously or on adding one or more seed crystals. The solution may then be held at a temperature of about 50° C. to allow crystallisation of product to occur. Subsequently, the solution may be cooled at a controlled rate to about 20° C. to allow crystallisation of product to finish. A suitable cooling rate is, for example, about 10° C. per hour. The crystalline AZD0530 trihydrate so obtained may be isolated by any conventional method, for example by filtration or centrifugation.

When one or more seed crystals are used to initiate nucleation in the crystallisation/recrystallisation processes described above, the seed crystals are preferably crystals of the AZD0530 trihydrate. The seed crystal(s) may be prepared using any suitable method for the preparation of AZD0530 trihydrate, for example by slurrying a sample of amorphous AZD0530 in water.

It will be appreciated by the man skilled in the art that the procedures described above may be varied using routine skill and knowledge. For example, provided that AZD0530 trihydrate is obtained substantially free of any other AZD0530 form, any of the quantity of the compound 4-(6-chloro-2,3-methylenedioxyanilino)-7-[2-(4-methylpiperazin-1-yl) ethoxy]-5-tetrahydropyran-4-yloxyquinazoline that is treated, the nature and volume of the solvent and any co-solvent, the ratio of the component solvents if a solvent mixture is employed, the volume of water used and the ratio of water to solvent and the temperatures of the dissolution and cooling phases may be varied. For example, nucleation of a solution of the compound of the Formula I in a suitable solvent, for example a (2-6C)alcohol such as ethanol in step (b) of the process may be induced by, for example, the evaporation of some of the ethanol solvent, alternatively, nucleation could be induced by the addition of a suitable antisolvent for the compound of Formula I, thereby creating supersaturation of the solution from which AZD0530 trihydrate crystallises.

The crystallisation process for preparing the AZD0530 trihydrate enables the trihydrate to be prepared in high purity. Furthermore, recrystallisation of the AZD0530 trihydrate so obtained may be carried out using the process described above. Recrystallisation offers the possibility for further purifying the material.

According to a further aspect of the present invention, there is provided a process for preparing a compound of the Formula I substantially in the form of AZD0530 trihydrate which comprises:—

(a) contacting 4-(6-chloro-2,3-methylenedioxyanilino)-7-[2-(4-methylpiperazin-1-yl)ethoxy]-5-tetrahydropyran-4-yloxyquinazoline with water for a sufficient time to form AZD0530 trihydrate; and (b) isolating the AZD0530 trihydrate.

The 4-(6-chloro-2,3-methylenedioxyanilino)-7-[2-(4-methylpiperazin-1-yl)ethoxy]-5-tetrahydropyran-4-yloxyquinazoline used as the starting material in process step (a) immediately above may be any form of the compound of Formula I, for example the amorphous form described in the prior art or any one of the crystalline forms described herein such as anhydrous AD0530.

Conveniently, conversion to AZD0530 trihydrate is effected by preparing a slurry of the 4-(6-chloro-2,3-methylenedioxyanilino)-7-[2-(4-methylpiperazin-1-yl)ethoxy]-5-tetrahydropyran-4-yloxyquinazoline starting material in water, optionally in the presence of one or more suitable organic solvent(s). Generally a molar excess of water is used to ensure substantially complete conversion of the 4-(6-chloro-2,3-methylenedioxyanilino)-7-[2-(4-methylpiperazin-1-yl)ethoxy]-5-tetrahydropyran-4-yloxyquinazoline starting material to the AZD0530 trihydrate (i.e. the molar ratio of water to quinazoline compound is at least 3:1). The upper limit of water concentration is not critical, however, generally a large molar excess of water is used. For example, the molar ratio of water to the quinazoline compound is suitably from about 3:1 to 1000:1 or more, particularly from about 3:1 to about 400:1.

In a particular embodiment, a slurry of the 4-(6-chloro-2,3-methylenedioxyanilino)-7-[2-(4-methylpiperazin-1-yl) ethoxy]-5-tetrahydropyran-4-yloxyquinazoline starting material is prepared in a mixture of water and an organic solvent, and optionally one or more co-solvents. We have found that the use of an organic solvent significantly reduces the time required to convert the starting material to AZD0530 trihydrate. Suitable organic solvents are water-miscible polar organic solvents, such as polar protic solvents, for example (1-4C)alcohols, particularly ethanol and isopropanol, polar non-protic solvents such as aliphatic esters, for example a (1-4C)alkyl (2-3C)alkanoate ester, particularly ethyl acetate, aliphatic (3-6C)ketones such as acetone or aliphatic amides such as N,N-dimethylformamide. Particular solvents include, for example, isopropanol or ethyl acetate, or a mixture thereof.

The amount of organic solvent used may be insufficient to completely dissolve the 4-(6-chloro-2,3-methylenedioxyanilino)-7-[2-(4-methylpiperazin-1-yl)ethoxy]-5-tetrahydropyran-4-yloxyquinazoline starting material such that a slurry is retained throughout the process. Conveniently, by retaining the compound of the Formula I in a slurry during the process, the AZD0530 trihydrate can be formed without the need to induce crystallisation by, for example, cooling the mixture or evaporating solvent. Accordingly, the slurry process may be operated at a substantially constant temperature.

Without wishing to be bound by theory, it is thought that the process proceeds via a mechanism of localised dissolution of the 4-(6-chloro-2,3-methylenedioxyanilino)-7-[2-(4-methylpiperazin-1-yl)ethoxy]-5-tetrahydropyran-4-yloxyquinazoline starting material and subsequent crystallisation of AZD0530 trihydrate. Hence, the slurry conversion process described herein is thought to be a portionwise dissolution and conversion of the starting material to AZD0530 trihydrate.

The specific amount of organic solvent used will be dependent upon the organic solvent selected and the conditions under which the slurry is contacted with the water. In the case of solvents such as isopropanol or ethyl acetate a range of 0.1 to 20 ml/g, such as 2 to 10 ml/g and particularly approximately 5 ml/g is suitable, wherein "ml/g" refers to the volume of organic solvent per g of the 4-(6-chloro-2,3-methylenedioxyanilino)-7-[2-(4-methylpiperazin-1-yl)ethoxy]-5-tetrahydropyran-4-yloxyquinazoline.

A single organic solvent may be used or two or more organic solvents, for example a mixture of ethyl acetate and isopropanol (suitably in a volume ratio of approximately 1:1), may be used, together with the water.

Optionally a co-solvent may be used. Suitable co-solvents include, for example, weakly polar organic solvents such as aromatic hydrocarbons (for example toluene), halogeno-(1-6C)alkanes (for example 1,2-dichloroethane) and aliphatic di-(1-6C)alkyl ethers or (4-7C)cyclic ethers (for example tetrahydrofuran). A particular co-solvent is toluene. A suitable ratio by volume of co-solvent (such as toluene) to organic solvent (such as isopropanol) lies within the range 50:1 to 0.05:1, conveniently in the range 10:1 to 0.5:1, and particularly from about 3:1 to 1:1.

Optionally, one or more seed crystals of AZD0530 trihydrate may be added to the slurry to enhance the rate of conversion to AZD0530 trihydrate.

The process is suitably carried out at about ambient temperature, for example from approximately 15 to 30° C., particularly approximately 20 to 25° C.

The time required for conversion to the AZD0530 trihydrate is dependent upon the particular reaction conditions used, such as temperature, presence of an organic solvent and whether seeding crystals are used. Generally, a reaction time of, for example, from 5 minutes to 48 hours is suitable.

We have also found that AZD0530 trihydrate can be readily converted to crystalline anhydrous AZD0530. Accordingly, crystallisation of AZD0530 trihydrate and subsequent conversion to anhydrous AZD0530 provides a means for preparing anhydrous AZD0530 in high purity. Such a process for the preparation of the compound of Formula I substantially in the form of anhydrous AZD0530 provides a further aspect of the present invention.

There is also provided a process for preparing a compound of the Formula I substantially in the form of crystalline anhydrous AZD0530 which comprises the step of dehydrating AZD0530 trihydrate.

One embodiment of this conversion, designated hereinafter as Conversion Process 1, comprises the step of passing a stream of substantially dry inert gas over and/or through a sample of AZD0530 trihydrate for a sufficient time and at sufficient temperature to drive off water and effect transformation to anhydrous AZD0530.

Conveniently, Conversion Process 1 is carried out at ambient temperature (a temperature in the range of from 15 to 25° C., particularly at about 20° C.). A suitable inert gas is, for example, nitrogen gas which should be dried if necessary until it is substantially dry. Generally, Conversion Process 1 requires a drying time of from 5 minutes to 50 hours, suitably 1 to 30 hours, to convert AZD0530 trihydrate to anhydrous AZD0530. Conveniently, the AZD0530 trihydrate may be placed on a filter and the drying gas may be passed through the filter. Suitably, the drying step in Conversion Process 1 should be continued for sufficient time to ensure substantially complete conversion to the desired anhydrous form. By substantially complete conversion is meant that at least 80% of the compound of the Formula I is in the form of anhydrous AZD0530 and less than 20% of any other AZD0530 form is present. Particularly, at least 90% and, in particular, at least 95% of the compound of the Formula I is in the form of anhydrous AZD0530. The degree of conversion to the required anhydrous AZD0530 may be assessed using routine techniques, for example XRPD as described herein.

Optionally, the stream of inert gas such as nitrogen is warmed prior to its passage over and/or through the material. A suitable temperature for the warmed gas is, for example, a temperature of from 25 to 100° C., particularly from 40 to 60° C.

A further embodiment of this conversion, designated hereinafter as Conversion Process 2, comprises the step of heating compound of the Formula I substantially in the form of AZD0530 trihydrate for a sufficient time and at sufficient temperature to drive off water and effect transformation to anhydrous AZD0530.

Conversion Process 2 is suitably carried out by heating AZD0530 trihydrate at a temperature of from 50 to 150° C., particularly from 80 to 140° C., more particularly from 120 to 130° C. The heating time required is dependent on, amongst other things, the size of the sample and the heating method employed. Generally a heating time of from 5 minutes to 100 hours, suitably 1 to 30 hours, is sufficient to convert AZD0530 trihydrate to anhydrous AZD0530. The AZD0530 trihydrate may be heated using conventional techniques, for example in a suitable oven or vacuum oven or in a conventional drying system such as a fluid bed dryer. Suitably, the heating step in Conversion Process 2 should be continued for sufficient time and at a sufficient temperature to ensure substantially complete conversion as defined hereinbefore to the desired anhydrous form.

A further embodiment of this conversion, designated hereinafter as Conversion Process 3, comprises:—
(a) washing compound of the Formula I substantially in the form of AZD0530 trihydrate with a solvent or solvent mixture substantially to remove water; and
(b) isolating the anhydrous AZD0530 so formed.

In Conversion Process 3, a suitable solvent includes, for example, water-miscible organic solvents in which the compound of the Formula I is sparingly soluble at the washing temperature. Examples of suitable solvents include, weakly polar organic solvents such as aliphatic di-(1-6C)alkyl ethers or (4-7C)cyclic ethers such as tetrahydrofuran, more polar protic solvents, for example (2-6C)alcohols such as ethanol and isopropanol, polar non-protic solvents such as (1-4C)alkyl (2-3C)alkanoate esters such as ethyl acetate and nitriles such as acetonitrile. Mixtures of such solvents may also be employed. A particular solvent is isopropanol and/or ethyl acetate.

It is to be understood that the 'washing' step requires a suitable period of time to effect conversion to the anhydrous AZD0530. A suitable contact time between the solid and washing solvent is in the range of about 5 minutes to 1 or more hours. More conveniently, the contact time is in the range of about 30 minutes to about 2 hours, for example about 1 hour. Conveniently, a slurry of the solid and the washing solvent is prepared. Conveniently, the slurry is stirred to improve contact between the washing solvent and the crystals of solid. The washing solvent may be warmed, for example to a temperature of about 30 to 50° C., however, generally washing at about ambient temperature is sufficient to effect conversion to anhydrous AZD0530.

Optionally, the material isolated following the solvent washing step(s) in Conversion Process 3 is dried to ensure complete removal of water and conversion to the desired crystalline anhydrous AZD0530. The methods of Conversion Process 1 or Conversion Process 2 may be employed.

The invention is illustrated hereinafter by means of the following Examples, data and Figures in which:—
(i) X-ray diffraction data were obtained using Siemens D5000 equipment. The sample was prepared by gently breaking up crystal aggregates using an agate pestle and mortar. The sample was filled into a standard holder (having a flat lip) and compressed flush to the lip with a glass microscope slide. The sample was spun at 30 revolutions per minute (rpm) to improve counting statistics. The X-rays were generated by a copper long-fine focus tube operated at 40 kV and 40 mA. The wavelength of the X-rays was 1.5406 Å. The instrument was operated in θ-θ configuration over the scan range 2° 2θ to 40° 2θ with 4 seconds exposure per 0.02° 2θ increment. The examinations were carried out in Bragg-Brentano configuration whereby the X-ray beam was passed through an automatic variable divergence slit at V20 and the reflected radiation directed through a 2 mm antiscatter slit and a 0.2 mm detector slit. The reflections are quoted as their centroid values (calculated by a computer package such as DIFFRAC/AT). Persons skilled in the art of XRPD will realise that analysis of samples with grains above 30 microns in size and non-unitary aspect ratios may affect the relative intensity of peaks. The skilled person will also realise that the position of reflections is affected by the precise height at which the sample sits in the diffractometer and the zero calibration of the diffractometer. The surface planarity of the sample may also have a small effect. Hence the diffraction pattern data presented are not to be taken as absolute values.

It will also be appreciated that different equipment and/or conditions may result in slightly different data being generated, for example there may be variation in the location and relative intensities of the peaks. Generally, a measurement error of peak location (diffraction angle) in an XRPD spectrum will be about plus or minus 0.3° 2θ. Such a degree of measurement error should be taken into account when it is assessed whether or not XRPD spectra are substantially the same. The person skilled in the art will understand that it is the relative position of the peaks rather than their precise individual peak locations that is a more reliable indicator of whether or not samples have arisen from substantially the same crystalline form. In particular, the intensities of peaks measured using XRPD may vary as a result of particle size and shape because of the effects of the packing of the crystalline particles into XRPD mounts. Such packing effects are well known in the art and are often referred to as the "preferred orientation" effect. Preferred orientation in the specimen influences the intensities of various reflections so that some are more intense and others less intense, compared to the intensity that would be expected from a completely random sample. The preferred orientation effect is especially evident for needle-like or plate-like crystals when size reduction yields finer needles or platelets. As a result, crystalline forms are most reliably characterised primarily by relative peak positions in the X-ray diffractogram. These effects as well as methods for standard X-ray diffraction analysis can be found in, for example, Bunn, C. W. (1948), Chemical Crystallography, Clarendon Press, London; or Klug, H. P. & Alexander, L. E. (1974), X-Ray Diffraction Procedures, John Wiley and Sons, New York. Hence, the figures quoted herein are not to be taken as absolute values. It should therefore be understood that any crystals providing an XRPD spectrum that is substantially the same as one of the XRPD spectra disclosed herein fall within the scope of the present invention.

(ii) Melting points and TGA were determined using Mettler DSC820e and Mettler TG851 equipment respectively using TSO891RO robotic systems.

For the melting point determination, the pan type was aluminium (40 μl size) with a pierced lid. The sample weight was approximately 1 to 5 mg. The procedure was carried out under a flow of nitrogen gas (100 ml/min) and the temperature range studied was 25° C. to 325° C. at a constant rate of temperature increase of 10° C. per minute. The skilled person will realise that the precise value of the melting point will be influenced by the purity of the compound, the sample weight, the heating rate and the particle size. It will therefore be appreciated that alternative readings of melting point may be given by other types of equipment or by using conditions different to those described. Hence the figures quoted herein should not to be taken as absolute values.

For the TGA determination, each sample (approximately 1 to 12 mg) was placed in an open aluminium oxide pan (70 μl size) and the procedure was carried out under a flow of helium gas (50 ml/min) and the temperature range studied was 25° C. to 325° C. at a constant rate of temperature increase of 10° C. per minute. It will be appreciated that slightly different data may be generated if different equipment and/or conditions are used. Hence the figures quoted herein should not to be taken as absolute values.

(iii) DRIFT spectroscopy data were obtained on a Nicolet 20SXC spectrometer, using a 2% w/w dispersion of the sample in powdered potassium bromide over the frequency range 4000 to 400 $cm^{-1}$. It will be appreciated that slightly different data may be generated if different equipment and/or conditions of sample preparation are used. Hence the figures quoted herein are not to be taken as absolute values.

BRIEF DESCRIPTION OF THE DRAWINGS

FIG. 1 shows the X-ray powder diffraction pattern for AZD0530 difumarate with the 2θ values plotted on the horizontal axis and the relative line intensity (Count) plotted on the vertical axis.

FIG. 2 shows the X-ray powder diffraction pattern for AZD0530 sesquifumarate tetrahydrate with the 2θ values plotted on the horizontal axis and the relative line intensity (Count) plotted on the vertical axis.

FIG. 3 shows the X-ray powder diffraction pattern for AZD0530 trihydrate with the 2θ values plotted on the horizontal axis and the relative line intensity (Count) plotted on the vertical axis.

FIG. 4 shows the X-ray powder diffraction pattern for anhydrous AZD0530 with the 2θ values plotted on the horizontal axis and the relative line intensity (Count) plotted on the vertical axis.

FIG. 5 shows the DRIFT spectrum for AZD0530 difumarate with the frequency range 4000 to 400 $cm^{-1}$ plotted on the horizontal axis and absorbance plotted on the vertical axis.

FIG. 6 shows the DRIFT spectrum for AZD0530 sesquifumarate tetrahydrate with the frequency range 4000 to 400 $cm^{-1}$ plotted on the horizontal axis and absorbance plotted on the vertical axis.

With regard to the following Examples, generally:

(i) operations were carried out at ambient temperature, i.e. in the range 17 to 25° C. and under an atmosphere of an inert gas such as nitrogen or argon unless otherwise stated;

(ii) in general, the course of reactions was followed by thin layer chromatography (TLC) and/or analytical high pressure liquid chromatography (HPLC); the reaction times that are given are not necessarily the minimum attainable;

(iii) when necessary, organic solutions were dried over anhydrous magnesium sulphate, work-up procedures were carried out after removal of residual solids by filtration, evaporations were carried out by rotary evaporation in vacuo;

(iv) yields, where present, are not necessarily the maximum attainable, and, when necessary, reactions were repeated if a larger amount of the reaction product was required;

(v) in general, the structures of the end-products of the Formula I were confirmed by nuclear magnetic resonance (NMR) and/or mass spectral techniques; electrospray mass spectral data were obtained using a Waters ZMD or Waters ZQ LC/mass spectrometer acquiring both positive and negative ion data, generally, only ions relating to the parent structure are reported; proton NMR chemical shift values were measured on the delta scale using a Bruker Spectrospin DPX300 spectrometer operating at a field strength of 300 MHz; the following abbreviations have been used: s, singlet; d, doublet; t, triplet; q, quartet; m, multiplet; br, broad;

(vi) intermediates were not necessarily fully purified but their structures and purity were assessed by TLC, analytical HPLC, infra-red (IR) and/or NMR analysis;

(vii) unless otherwise stated, column chromatography (by the flash procedure) and medium pressure liquid chromatography (MPLC) were performed on Merck Kieselgel silica (Art. 9385);

(viii) preparative HPLC was performed on C18 reversed-phase silica, for example on a Waters 'Xterra' preparative reversed-phase column (5 microns silica, 19 mm diameter, 100 mm length) using decreasingly polar mixtures as eluent, for example decreasingly polar mixtures of water (containing 1% acetic acid or 1% aqueous ammonium hydroxide (d=0.88) and acetonitrile;

(ix) the following analytical HPLC methods were used; in general, reversed-phase silica was used with a flow rate of about 1 ml per minute and detection was by UV absorbance at a wavelength of 230 nm:—

Method A: Phenomenex LUNA phenylhexyl column ((Phenomenex, Macclesfield, UK; 3 microns silica, 2 mm diameter, 50 mm length), Solvent A was water containing 0.05% trifluoroacetic acid and Solvent B was methanol containing 0.05% trifluoroacetic acid, and a solvent gradient over 5 minutes from a 95:5 mixture of Solvents A and B to a 0:100 mixture of Solvents A and B was employed;

Method B: Phenomenex PRODIGY ODS column (5 microns silica, 4.6 mm diameter, 150 mm length), Solvent A was a 900:100:0.5:0.5 mixture of water, acetonitrile, trifluoroacetic acid and acetic acid and Solvent B was 50:950:0.5:0.5 mixture of water, acetonitrile, trifluoroacetic acid and acetic acid, and a solvent gradient over 8 minutes from 100% Solvent A to a 60:40 mixture of Solvents A and B and a further solvent gradient over 10 minutes from a 60:40 mixture of Solvents A and B to 100% Solvent B was employed.

EXAMPLE 1

5,7-difluoro-3,4-dihydroquinazolin-4-one (Route 1)

2,4,6-Trifluorobenzonitrile (10 g) was added to a stirred 4.9M ammonia solution in isopropanol (220 ml; prepared by bubbling ammonia through isopropanol) and the resultant mixture was heated to 45° C. for 16 hours. The solvent was evaporated to leave a white solid (11.9 g) comprising a 2:1 mixture of 2-amino-4,6-difluorobenzonitrile and 4-amino-2,6-difluorobenzonitrile.

A portion (5 g) of the mixture was suspended in water (10 ml) and concentrated aqueous sulphuric acid (80%; 40 ml) was added. The resultant mixture was stirred and heated to 65° C. for 16 hours. The resultant solution was cooled to ambient temperature, diluted with water (60 ml), basified by the addition of 10M aqueous sodium hydroxide (180 ml) and extracted with ethyl acetate. The organic solution was dried over magnesium sulphate and evaporated. There was thus obtained a cream solid (4 g) comprising a 2:1 mixture of 2-amino-4,6-difluorobenzamide and 4-amino-2,6-difluorobenzamide.

The mixture so obtained was suspended in triethyl orthoformate (60 ml). Concentrated aqueous hydrochloric acid (0.1 ml) was added and the resultant mixture was heated to 146° C. for 8 hours. The reaction mixture was allowed to cool to ambient temperature. The resultant thick suspension was filtered and washed with methyl tert-butyl ether (20 ml). The material so obtained was dried in vacuo at 35° C. for 3 hours. There was thus obtained 5,7-difluoro-3,4-dihydroquinazolin-4-one (1.61 g; 97% HPLC purity using Method A, retention time 2.29 minutes); NMR Spectrum: (DMSOd$_6$) 7.3-7.4 (m, 2H), 8.12 (s, 1H).

EXAMPLE 2

5,7-difluoro-3,4-dihydroquinazolin-4-one (Route 2)

A portion (0.5 g) of the 2:1 mixture of 2-amino-4,6-difluorobenzonitrile and 4-amino-2,6-difluorobenzonitrile described in Example 1 was purified by column chromatography on silica using increasingly polar mixtures of methylene chloride and methanol as eluent. There was thus obtained 2-amino-4,6-difluorobenzonitrile (0.15 g). A mixture of the material so obtained, concentrated aqueous sulphuric acid (80%; 4 ml) and water (1 ml) was heated to 100° C. for 15 hours. The resultant solution was cooled to ambient temperature, diluted with water and basified by the addition of 10M aqueous sodium hydroxide solution and washed with ethyl acetate (10 ml). The resultant aqueous solution was neutralised by the addition of dilute aqueous hydrochloric acid solution and extracted with ethyl acetate (20 ml). The organic layer was dried over magnesium sulphate and evaporated. There was thus obtained 2-amino-4,6-difluorobenzoic acid as a colourless solid (0.11 g; 97% HPLC purity using Method B, retention time 6.87 minutes); NMR Spectrum: (DMSOd$_6$) 6.25 (m, 1H), 6.4 (m, 1H).

A mixture of the material so obtained, 1,3,5-triazene (0.044 g), methanol (4 ml) and piperidine (0.038 ml) was heated to 70° C. for 24 hours. The resultant mixture was cooled to ambient temperature and evaporated. Diethyl ether (3 ml) and ethyl acetate (1 ml) were added and the resultant solid was isolated and washed with diethyl ether (1 ml). There was thus obtained 5,7-difluoro-3,4-dihydroquinazolin-4-one (0.048 g).

EXAMPLE 3

7-fluoro-5-tetrahydropyran-4-yloxy-3,4-dihydroquinazolin-4-one

Potassium tert-butoxide (6.15 g) was added to a solution of 4-hydroxytetrahydropyran (2.94 g) in THF (40 ml) and the mixture was stirred at ambient temperature for 15 minutes. The resultant mixture was added to a stirred solution of 5,7-difluoro-3,4-dihydroquinazolin-4-one (5 g) in THF (60 ml) that was being heated to reflux. A further portion of THF (20 ml) was added and the reaction mixture was heated to reflux for 30 minutes. A second portion of potassium tert-butoxide (6.15 g) was added and the reaction mixture was heated to reflux for 40 minutes. A third portion of potassium tert-butoxide (1.52 g) was added and the reaction mixture was heated to reflux for 20 minutes. The reaction mixture was allowed to cool to ambient temperature. Water (50 ml) was added and the bulk of the organic solvent was evaporated. The residue was acidified to pH<2 by the dropwise addition of 2M aqueous hydrochloric acid. The resultant slurry was stirred for 15 minutes. The mixture was filtered and the isolated solid was washed with water (20 ml) and dried overnight in vacuo at 40° C. There was thus obtained 7-fluoro-5-tetrahydropyran-4-yloxy-3,4-dihydroquinazolin-4-one (5.96 g; 96% HPLC purity using Method A, retention time 3.34 minutes); NMR Spectrum: (DMSOd$_6$) 1.6-1.75 (m, 2H), 1.9-2.0 (m, 2H), 3.5-3.6 (m, 2H), 3.85-3.95 (m, 2H), 4.8 (m, 1H), 6.9 (m, 1H), 7.05 (m, 1H), 8.0 (s, 1H).

EXAMPLE 4

7-[2-(4-methylpiperazin-1-yl)ethoxy]-5-tetrahydropyran-4-yloxy-3,4-dihydroquinazolin-4-one Potassium tert-butoxide (3.77 g) was added to a solution of 1-(2-hydroxyethyl)-4-methylpiperazine (International Application WO 01/94341, Example 2, Note [9]; 1.78 g) in THF (30 ml) and the mixture was stirred for 10 minutes. The resultant solution was added to a stirred slurry of 7-fluoro-5-tetrahydropyran-4-yloxy-3,4-dihydroquinazolin-4-one (2.96 g) in THF (50 ml) and the resultant solution was heated to reflux for 3 hours. A second portion of potassium tert-butoxide (2.52 g) was added and the reaction mixture was heated to reflux for 16 hours. The reaction mixture was allowed to cool to ambient temperature. Water (25 ml) was added and the bulk of the organic solvent was evaporated. The residue was neutralised by the dropwise addition of 2M aqueous hydrochloric acid and extracted with ethyl acetate. The organic phase was dried over magnesium sulphate and evaporated. The residue was purified by column chromatography on silica using increasingly polar mixtures of methylene chloride and methanol as eluent. There was thus obtained 7-[2-(4-methylpiperazin-1-yl)ethoxy]-5-tetrahydropyran-4-yloxy-3,4-dihydroquinazolin-4-one (3.1 g; 91% HPLC purity using Method B, retention time 1.1 minutes); NMR Spectrum: (CDCl$_3$) 1.9-2.0 (m, 2H), 2.0-2.15 (m, 2H), 2.35 (s, 3H), 2.4-2.8 (br m, 8H), 2.85 (t, 2H), 3.6-3.7 (m, 2H), 4.1-4.15 (m, 2H), 4.2 (t, 2H), 4.65 (m, 1H), 6.55 (s, 1H), 6.85 (s, 1H), 7.25 (s, 1H), 7.9 (s, 1H).

EXAMPLE 5

4-(6-chloro-2,3-methylenedioxyanilino)-5,7-difluoroquinazoline (Route 1)

Phosphoryl chloride (3.32 ml) was added to a stirred mixture of 5,7-difluoro-3,4-dihydroquinazolin-4-one (5 g), diisopropylethylamine (7.16 ml) and acetonitrile (120 ml) that was cooled in an ice bath. The resultant reaction mixture was heated to 80° C. for 2 hours. A second portion of phosphoryl chloride (1.52 ml) was added and the reaction mixture was heated to reflux for a further 2.75 hours to provide a solution of 4-chloro-5,7-difluoroquinazoline which was used without being isolated. A solution of 6-chloro-2,3-methylenedioxyaniline (International Application WO 01/94341, Example 17, Note [30]; 4.95 g) in acetonitrile (15 ml) was added and the reaction mixture was heated to 80° C. for 4 hours. The resultant reaction mixture was stirred at ambient temperature for 16 hours. A solution of a second portion of 6-chloro-2,3-methylenedioxyaniline (1.18 g) in acetonitrile (5 ml) was added and the reaction mixture was reheated to 80° C. for 1 hour. The reaction mixture was allowed to cool to ambient temperature and was stirred for one hour. The resultant slurry was filtered and the isolated solid was washed with acetonitrile (20 ml) and dried. There was thus obtained 4-(6-chloro-2,3-methylenedioxyanilino)-5,7-difluoroquinazoline as a monohydrochloride salt (7.88 g, 99.3% HPLC purity using Method A, retention time 4.46 minutes); NMR Spectrum: (DMSOd$_6$) 5.5-6.0 (br s, 1H), 6.15 (s, 2H), 7.0 (d, 1H), 7.1 (d, 1H), 7.6 (d, 1H), 7.8 (m, 1H), 8.7 (s, 1H), 1.9-2.0 (m, 2H).

EXAMPLE 6

4-(6-chloro-2,3-methylenedioxyanilino)-5,7-difluoroquinazoline (Route 2)

Trimethylaluminium (2M solution in toluene, 4.69 ml) was added to a stirred solution of 6-chloro-2,3-methylenedioxyaniline (1.07 g) in toluene (10 ml) and the resultant solution was stirred at ambient temperature for 15 minutes. A solution of 2,4,6-trifluorobenzonitrile (0.98 g) in toluene (10 ml) was added dropwise and the resultant mixture was stirred at ambient temperature for 10 minutes and then heated to 90° C. for 3 hours. The reaction mixture was cooled to ambient temperature and stirred for 16 hours. The reaction mixture was washed with water (20 ml). The organic solution was extracted with 10% aqueous citric acid solution. The aqueous solution was basified with 2M aqueous sodium hydroxide and extracted with methylene chloride (50 ml). The organic solution was dried over magnesium sulphate and evaporated. There was thus obtained N$^1$-(6-chloro-2,3-methylenedioxyphenyl)-2,4,6-trifluorobenzamidine (0.92 g).

Formamidine acetic acid salt (0.185 g) was added to a stirred solution of N$^1$-(6-chloro-2,3-methylenedioxyphenyl)-2,4,6-trifluorobenzamidine (0.204 g) in toluene (5 ml) and the reaction mixture was heated to reflux for 16 hours. A second portion (0.185 g) of formamidine acetic acid salt was added and the reaction mixture was heated to reflux for a further 16 hours. Triethylamine (0.25 ml) was added and the reaction mixture was heated to reflux for a further 3 days. The resultant reaction mixture was cooled to ambient temperature and partitioned between methylene chloride (25 ml) and a saturated aqueous sodium bicarbonate solution (25 ml). The organic solution was washed with 10% aqueous citric acid (25 ml), dried over magnesium sulphate and evaporated. The resultant oil was purified by column chromatography on silica gel using increasingly polar mixtures of isohexane and ethyl acetate as eluent. There was thus obtained 4-(6-chloro-2,3-methylenedioxyanilino)-5,7-difluoroquinazoline (0.068 g).

EXAMPLE 7

4-(6-chloro-2,3-methylenedioxyanilino)-5,7-difluoroquinazoline

Phosphoryl chloride (4.96 ml) was added over a period of 40 minutes to a stirred mixture of 5,7-difluoro-3,4-dihydroquinazolin-4-one (6.5 g), chlorobenzene (64.9 ml), 6-chloro-2,3-methylenedioxyaniline (7.08 g) and diisopropylethylamine (7.47 ml) that had been heated to 95° C. under an atmosphere of nitrogen gas. The resultant reaction mixture was heated at 95° C. for 5 hours. The reaction mixture was cooled to 18° C. and stirred for 30 minutes. Stirring was stopped and the reaction mixture was allowed to stand for 30 minutes. The mixture was filtered and the isolated solid was washed with chlorobenzene (2×23 ml) and dried in vacuo at 45° C. There was thus obtained 4-(6-chloro-2,3-methylenedioxyanilino)-5,7-difluoroquinazoline as a mono-hydrochloride salt (8.9 g, 96.5% HPLC purity using Method A, retention time 4.46 minutes); m.p. 234-237° C.; NMR Spectrum: (DMSOd$_6$) 5.5-6.0 (br s, 1H), 6.15 (s, 2H), 7.0 (d, 1H), 7.1 (d, 1H), 7.6 (d, 1H), 7.8 (m, 1H), 8.7 (s, 1H).

EXAMPLE 8

4-(6-chloro-2,3-methylenedioxyanilino)-7-fluoro-5-tetrahydropyran-4-yloxyquinazoline (Route 1)

A first portion (0.25 g) of 7-fluoro-5-tetrahydropyran-4-yloxy-3,4-dihydroquinazolin-4-one was added to a stirred mixture of phosphoryl chloride (1.76 ml), diisopropylethylamine (3.95 ml) and acetonitrile (10 ml) that had been heated to 80° C. The resultant mixture was heated to 80° C. for 3 hours. A second portion (0.25 g) of 7-fluoro-5-tetrahydropyran-4-yloxy-3,4-dihydroquinazolin-4-one was added and the mixture was heated to reflux for a further 90 minutes. There was thus obtained a solution of 4-chloro-7-fluoro-5-tetrahydropyran-4-yloxyquinazoline which was used without being isolated. A solution of 6-chloro-2,3-methylenedioxyaniline (0.32 g) in acetonitrile (3 ml) was added and the reaction mixture was heated to 80° C. for 2.5 hours. As the required conversion was incomplete, the reaction mixture was evaporated and toluene (15 ml) was added as reaction solvent. A second portion of 6-chloro-2,3-methylenedioxyaniline (0.32 g) was added and the reaction mixture was heated to reflux for 3 hours. The reaction mixture was cooled to ambient temperature and partitioned between methylene chloride and an aqueous sodium chloride solution. The organic phase was washed with water, dried over magnesium sulphate and evaporated. There was thus obtained 4-(6-chloro-2,3-methylenedioxyanilino)-7-fluoro-5-tetrahydropyran-4-yloxyquinazoline as a foam (0.73 g); NMR Spectrum: (DMSOd$_6$) 1.9-2.05 (m, 2H), 2.1-2.2 (m, 2H), 3.5-3.6 (m, 2H), 3.8-3.95 (m, 2H), 5.1 (m, 1H), 6.1 (s, 2H), 7.0 (d, 1H), 7.1 (d, 1H), 7.3 (d, 1H), 7.4 (m, 1H), 8.6 (s, 1H), 9.3 (s, 1H).

EXAMPLE 9

4-(6-chloro-2,3-methylenedioxyanilino)-7-fluoro-5-tetrahydropyran-4-yloxyquinazoline (Route 2)

A mixture of potassium tert-butoxide (5.42 g) and THF (30 ml) was added to a solution of 4-hydroxytetrahydropyran (1.53 ml) in THF (30 ml) and the resultant mixture was stirred for 20 minutes. A slurry of 4-(6-chloro-2,3-methylenedioxyanilino)-5,7-difluoroquinazoline hydrochloride salt (6 g) in THF (30 ml) was added and the resultant mixture was heated to reflux for 1.75 hours. A second portion (1.81 g) of potassium tert-butoxide was added and the mixture was heated to reflux for an additional 2 hours. A second portion (0.15 ml) of 4-hydroxytetrahydropyran and a third portion (0.45 g) of potassium tert-butoxide were added and the mixture was heated to reflux for 0.5 hours. A fourth portion (0.9 g) of potassium tert-butoxide was added and the mixture was heated to reflux for a further 20 minutes. The resultant reaction mixture was allowed to cool to 50° C. and brine (60 ml) and water (30 ml) were added in turn. The layers were separated and the aqueous solution was extracted in turn with THF (30 ml) and with isopropyl acetate (30 ml). The organic extracts were combined and washed with brine (30 ml). The organic solution was evaporated. The residual solid was stirred for 1 hour under a mixture of methyl tert-butyl ether (24 ml) and isohexane (12 ml). The solid was isolated, washed with a 1:1 mixture of methyl tert-butyl ether and isohexane and dried in vacuo overnight at 40° C. There was thus obtained 4-(6-chloro-2,3-methylenedioxyanilino)-7-fluoro-5-tetrahydropyran-4-yloxyquinazoline (5.02 g, 93% HPLC purity using Method A, retention time 4.61 minutes). A portion (3 g) of the material so obtained was dissolved in hot ethyl acetate (54 ml). The hot solution was filtered. The filtrate was allowed to cool to ambient temperature and was stirred for 3 hours. The resultant solid was isolated by filtration, and dried in vacuo at ambient temperature. There was thus obtained 4-(6-chloro-2,3-methylenedioxyanilino)-7-fluoro-5-tetrahydropyran-4-yloxyquinazoline (1.61 g, 99.2% HPLC purity using Method A, retention time 4.51 minutes); NMR Spectrum: (DMSOd$_6$) 1.9-2.0 (m, 2H), 2.1-2.2 (m, 2H), 3.5-3.6 (m, 2H), 3.8-3.95 (m, 2H), 5.1 (m, 1H), 6.1 (s, 2H), 6.95 (d, 1H), 7.1 (d, 1H), 7.2 (d, 1H), 7.3 (d, 1H), 8.4 (s, 1H), 9.3 (s, 1H).

EXAMPLE 10

4-(6-chloro-2,3-methylenedioxyanilino)-7-fluoro-5-tetrahydropyran-4-yloxyquinazoline (Route 3)

4-(6-Chloro-2,3-methylenedioxyanilino)-5,7-difluoroquinazoline hydrochloride salt (80 g) was added portionwise to a stirred mixture of sodium tert-pentoxide (90.2 g) and N-methylpyrrolidin-2-one (500 ml) under an atmosphere of nitrogen gas. 4-Hydroxytetrahydropyran (23.5 ml) and N-methylpyrrolidin-2-one (35 ml) were added and the resultant mixture was heated to 60° C. for 3 hours. Water (764 ml) was added to the heated reaction mixture during 3 hours and the mixture was stirred and heated to 60° C. for a further 3 hours. The warm reaction mixture was filtered and the isolated solid was washed with water (2×230 ml) and dried in vacuo to constant weight. There was thus obtained 4-(6-chloro-2,3-methylenedioxyanilino)-7-fluoro-5-tetrahydropyran-4-yloxyquinazoline (68.6 g, 95% HPLC purity using Method A, retention time 4.6 minutes); m.p. 209-212° C.; NMR Spectrum: (DMSOd$_6$) 1.9-2.0 (m, 2H), 2.1-2.2 (m, 2H), 3.5-3.6 (m, 2H), 3.8-3.95 (m, 2H), 5.05 (m, 1H), 6.1 (s, 2H), 6.95 (d, 1H), 7.05 (d, 1H), 7.1 (d, 1H), 7.3 (d, 1H), 8.4 (s, 1H), 9.3 (s, 1H).

EXAMPLE 11

4-(6-chloro-2,3-methylenedioxyanilino)-7-[2-(4-methylpiperazin-1-yl)ethoxy]-5-tetrahydropyran-4-yloxyquinazoline (Route 1)

A first portion of 7-[2-(4-methylpiperazin-1-yl)ethoxy]-5-tetrahydropyran-4-yloxy-3,4-dihydroquinazolin-4-one (0.19 g) in toluene (3 ml) was added to a stirred mixture of phosphoryl chloride (0.059 ml), diisopropylethylamine (0.13 ml) and toluene (3 ml) that was heated to 80° C. and the resultant mixture was heated to 80° C. for 6 hours. The mixture was allowed to cool to ambient temperature and was stirred overnight. The mixture was re-heated to 80° C. and a solution of 6-chloro-2,3-methylenedioxyaniline (0.088 g) in toluene (2 ml) was added. The resultant mixture was stirred and heated to 80° C. for 1.5 hours. The mixture was cooled to ambient temperature and the solvent was decanted from the oily gum that had been deposited. The oily gum was suspended in DMF (3 ml), a second portion of 7-[2-(4-methylpiperazin-1-yl)ethoxy]-5-tetrahydropyran-4-yloxy-3,4-dihydroquinazolin-4-one (0.088 g) was added and the reaction mixture was heated to 100° C. for 9 hours. The mixture was allowed to cool to ambient temperature and partitioned between ethyl acetate and a 2M aqueous hydrochloric acid solution (10 ml). The aqueous solution was basified by the addition of 10M aqueous sodium hydroxide solution (10 ml) and extracted with methylene chloride. The organic solution was dried over magnesium sulphate and evaporated. The resultant oil was purified by column chromatography on silica using increasingly polar mixtures of methylene chloride and methanol as eluent. There was thus obtained 4-(6-chloro-2,3-methylenedioxyanilino)-7-[2-(4-methylpiperazin-1-yl)ethoxy]-5-tetrahydropyran-4-yloxyquinazoline (0.008 g); NMR Spectrum: (DMSOd$_6$) 1.85-1.95 (m, 2H), 2.1-2.2 (m, 2H), 2.2 (s, 3H), 2.2-2.4 (m, 4H), 2.4-2.6 (m, 4H), 2.87 (m, 2H), 3.5-3.6 (m, 2H), 3.8-3.9 (m, 2H), 4.2 (m, 2H), 5.1 (m, 1H), 6.1 (s, 2H), 6.85 (s, 1H), 6.9 (s, 1H), 6.95 (d, 1H), 7.05 (d, 1H), 8.35 (s, 1H), 9.2 (s, 1H).

EXAMPLE 12

4-(6-chloro-2,3-methylenedioxyanilino)-7-[2-(4-methylpiperazin-1-yl)ethoxy]-5-tetrahydropyran-4-yloxyquinazoline (Route 2)

Under an atmosphere of nitrogen gas, phosphoryl chloride (0.07 ml) was added to a stirred mixture of 7-[2-(4-methylpiperazin-1-yl)ethoxy]-5-tetrahydropyran-4-yloxy-3,4-dihydroquinazolin-4-one (0.2 g), diisopropylethylamine (0.22 ml) and butyronitrile (2 ml) that had been heated to 96° C. and the resultant mixture was heated to 96° C. for 4 hours. A second portion (0.12 ml) of phosphoryl chloride was added and the resultant mixture was heated to 96° C. for 1.7 hours. 6-Chloro-2,3-methylenedioxyaniline (0.098 g) was added and the resultant mixture was heated to 96° C. for 2 hours. The mixture was allowed to cool to ambient temperature. Water (2 ml) was added and the organic layer was separated. The aqueous layer was washed with butyronitrile (1 ml). The aqueous layer was basified to pH9 by the addition of concentrated aqueous sodium hydroxide solution (47% w/w) and extracted with n-butanol (2×2 ml). The resultant organic layers were combined and evaporated. There was thus obtained 4-(6-chloro-2,3-methylenedioxyanilino)-7-[2-(4-methylpiperazin-1-yl)ethoxy]-5-tetrahydropyran-4-yloxyquinazoline (0.094 g).

EXAMPLE 13

4-(6-chloro-2,3-methylenedioxyanilino)-7-[2-(4-methylpiperazin-1-yl)ethoxy]-5-tetrahydropyran-4-yloxyquinazoline (Route 3)

4-(6-Chloro-2,3-methylenedioxyanilino)-7-fluoro-5-tetrahydropyran-4-yloxyquinazoline (0.5 g) was added to a stirred mixture of potassium hydroxide (0.168 g), 1-(2-hydroxyethyl)-4-methylpiperazine (0.69 g) and di-(2-methoxyethyl)ether (10 ml) that had been warmed to 120° C. and the resultant reaction mixture was heated to 120° C. for 12 hours. The reaction mixture was cooled to ambient temperature, acidified to pH 1 to 3 by the addition of 1M aqueous hydrochloric acid (9 ml) and washed with isopropyl acetate (20 ml). The aqueous solution was stirred and basified to pH 13 to 14 by the addition of 2M aqueous sodium hydroxide (5 ml). After 10 minutes, water (22 ml) was added and the mixture was stirred for 2 hours to allow precipitation of a solid to finish. The mixture was cooled to 10° C. and filtered. The resultant solid was washed with water (20 ml) and dried in vacuo at 40° C. There was thus obtained 4-(6-chloro-2,3-methylenedioxyanilino)-7-[2-(4-methylpiperazin-1-yl)ethoxy]-5-tetrahydropyran-4-yloxyquinazoline (0.47 g, 92.5% purity by HPLC using Method B, retention time 7.3 minutes); NMR Spectrum: ($CDCl_3$) 1.65 (br s, 3H), 1.9-2.05 (m, 2H), 2.2-2.3 (m, 2H), 2.31 (s, 3H), 2.4-2.8 (m, 8H), 2.9 (m, 2H), 3.6-3.7 (m, 2H), 3.95-4.05 (m, 2H), 4.2-4.25 (m, 2H), 4.8 (m, 1H), 6.05 (s, 2H), 6.55 (s, 1H), 6.75 (d, 1H), 6.85 (s, 1H), 7.0 (d, 1H), 8.55 (s, 1H), 9.25 (s, 1H).

EXAMPLE 14

4-(6-chloro-2,3-methylenedioxyanilino)-7-[2-(4-methylpiperazin-1-yl)ethoxy]-5-tetrahydropyran-4-yloxyquinazoline (Route 4)

Under an atmosphere of nitrogen gas, 1-(2-hydroxyethyl)-4-methylpiperazine (13.93 g) was added to a stirred mixture of 4-(6-chloro-2,3-methylenedioxyanilino)-7-fluoro-5-tetrahydropyran-4-yloxyquinazoline (12.9 g), sodium tert-pentoxide (9.87 g) and 1,2-diethoxyethane (37.5 ml). Water (1.34 g) and 1,2-diethoxyethane (25 ml) were added and the resultant reaction mixture was stirred and heated to 86° C. for 18 hours. The reaction mixture was cooled to 50° C. and, under vacuum distillation at approximately 60 millibar pressure, approximately 50 ml of reaction solvent was distilled off. The reaction mixture was neutralised to pH 7.0 to 7.6 by the addition of a mixture of concentrated aqueous hydrochloric acid (36%, 10 ml) and water (84 ml) at a rate that kept the temperature of the reaction mixture at a maximum of 60° C. With the temperature of the reaction mixture being kept at 60° C., the reaction mixture was extracted with ethyl acetate (225 ml). The organic solution was washed with water (50 ml). Water (25 ml) was added and, with the temperature being kept at 60° C., the mixture was stirred for 10 minutes, then allowed to stand for 30 minutes and the aqueous layer was separated. The organic layer was concentrated to a volume of about 100 ml by distillation of solvent at about 90° C. under atmospheric pressure. The residual mixture was cooled during 1 hour to 45° C. and held at that temperature for 2 hours to allow crystallisation of product. The mixture was warmed briefly to 55° C. and then cooled during 4 hours to 18° C. and held at that temperature for 1 hour. The crystalline precipitate was isolated by filtration and washed in turn with water (17 ml) and with tert-butyl methyl ether (17 ml). There was thus obtained 4-(6-chloro-2,3-methylenedioxyanilino)-7-[2-(4-methylpiperazin-1-yl)ethoxy]-5-tetrahydropyran-4-yloxyquinazoline as a trihydrate (11 g; 88% purity by HPLC using Method B, retention time 7.3 minutes); NMR Spectrum: ($CDCl_3$) 1.65 (br s, 3H), 1.9-2.05 (m, 2H), 2.2-2.3 (m, 2H), 2.31 (s, 3H), 2.4-2.8 (m, 8H), 2.9 (m, 2H), 3.6-3.7 (m, 2H), 3.95-4.05 (m, 2H), 4.2-4.25 (m, 2H), 4.8 (m, 1H), 6.05 (s, 2H), 6.55 (s, 1H), 6.75 (d, 1H), 6.85 (s, 1H), 7.0 (d, 1H), 8.55 (s, 1H), 9.25 (s, 1H).

A portion (10 g) of the material so obtained was placed on a filter and dried at ambient temperature in a stream of dry nitrogen gas. The resultant material was dissolved at 60° C. in dry isopropanol (140 ml) whilst maintaining a dry nitrogen atmosphere. The solution was allowed to cool to ambient temperature and to stand under a dry nitrogen atmosphere for 2 days. The resultant crystalline solid was isolated by filtration under a dry nitrogen atmosphere. The material (8 g) so obtained was a crystalline anhydrous form of 4-(6-chloro-2,3-methylenedioxyanilino)-7-[2-(4-methylpiperazin-1-yl)ethoxy]-5-tetrahydropyran-4-yloxyquinazoline, m.p. 142 to 144° C.

EXAMPLE 15

4-(6-chloro-2,3-methylenedioxyanilino)-7-[2-(4-methylpiperazin-1-yl)ethoxy]-5-tetrahydropyran-4-yloxyquinazoline difumarate salt A mixture of 4-(6-chloro-2,3-methylenedioxyanilino)-7-[2-(4-methylpiperazin-1-yl)ethoxy]-5-tetrahydropyran-4-yloxyquinazoline trihydrate (27.1 g), isopropanol (200 ml) and water (10 ml) was heated to 75° C. A mixture of fumaric acid (12.8 g), isopropanol (200 ml) and water (40 ml) was heated to 80° C.

A portion (80 ml) of the warmed solution of the quinazoline compound was added to the fumaric acid solution whilst the temperature was maintained at 75° C. The resultant mixture was stirred at 75° C. for 75 minutes. The remainder of the quinazoline compound solution was added during 1 hour whilst the temperature was maintained at 75° C. Isopropanol (50 ml) was added and the resultant mixture was stirred at 75° C. for 7 hours.

The mixture was cooled slowly over at least 25 minutes to 50° C. and was stirred at that temperature for 6 hours. The mixture was cooled slowly over at least 20 minutes to 20° C. and was stirred at that temperature for 18.5 hours. The crystalline solid was isolated by filtration, washed twice with a 10:1 mixture of isopropanol and water (50 ml and 100 ml respectively) and dried in vacuo at 45° C. to constant weight. There was thus obtained 4-(6-chloro-2,3-methylenedioxyanilino)-7-[2-(4-methylpiperazin-1-yl)ethoxy]-5-tetrahydropyran-4-yloxyquinazoline difumarate salt (37.0 g); m.p. 233-237° C.; NMR Spectrum: ($DMSOd_6$) 1.76-1.88 (m, 2H), 2.1-2.17 (m, 2H), 2.33 (s, 3H), 2.6 (br s, 8H), 2.78 (t, 2H), 3.51-3.6 (m, 2H), 3.83-3.9 (m, 2H), 4.24 (t, 2H), 4.98-5.07 (m, 1H), 6.07 (s, 2H), 6.6 (s, 4H), 6.83 (d, 1H), 6.84 (d, 1H), 6.91 (d, 1H), 7.05 (d, 1H), 8.33 (s, 1H), 9.18 (s, 1H).

EXAMPLE 16

4-(6-chloro-2,3-methylenedioxyanilino)-7-[2-(4-methylpiperazin-1-yl)ethoxy]-5-tetrahydropyran-4-yloxyquinazoline difumarate salt A mixture of 4-(6-chloro-2,3-methylenedioxyanilino)-7-[2-(4-methylpiperazin-1-yl)ethoxy]-5-tetrahydropyran-4-yloxyquinazoline trihydrate (27.1 g), isopropanol (210 ml) and water (30 ml) was heated to 40° C. and the mixture was filtered. The filter was washed with isopropanol (20 ml) and the washings were added to the warm filtrate. The resultant solution was warmed to 75° C.

A mixture of fumaric acid (12.8 g), isopropanol (200 ml) and water (20 ml) was heated to 70° C. and the resultant mixture was filtered. A portion (110 ml) of the fumaric acid solution was added to the warmed solution of 4-(6-chloro-2,3-methylenedioxyanilino)-7-[2-(4-methylpiperazin-1-yl)

ethoxy]-5-tetrahydropyran-4-yloxyquinazoline whilst the temperature was maintained at 75° C. Seed crystals of 4-(6-chloro-2,3-methylenedioxyanilino)-7-[2-(4-methylpiperazin-1-yl)ethoxy]-5-tetrahydropyran-4-yloxyquinazoline difumarate salt (0.02 g) were added and the resultant mixture was stirred at 75° C. for 1 hour. The remainder of the fumaric acid solution was added during 1 hour whilst the temperature was maintained at 75° C. and the resultant mixture was stirred at 75° C. for 14 hours.

The mixture was cooled slowly over at least 2 hours to 20° C. and was stirred at that temperature for 1 hour. The crystalline solid was isolated by filtration, washed twice with a 10:1 mixture of isopropanol and water (50 min and 100 ml respectively) and dried in vacuo at 45° C. to constant weight. There was thus obtained 4-(6-chloro-2,3-methylenedioxyanilino)-7-[2-(4-methylpiperazin-1-yl)ethoxy]-5-tetrahydropyran-4-yloxyquinazoline difumarate salt (35.8 g); m.p. 234-237° C.; NMR Spectrum: (DMSOd$_6$) 1.76-1.88 (m, 2H), 2.1-2.17 (m, 2H), 2.33 (s, 3H), 2.6 (br s, 8H), 2.78 (t, 2H), 3.51-3.6 (m, 2H), 3.83-3.9 (m, 2H), 4.24 (t, 2H), 4.98-5.07 (m, 1H), 6.07 (s, 2H), 6.6 (s, 4H), 6.83 (d, 1H), 6.84 (d, 1H), 6.91 (d, 1H), 7.05 (d, 1H), 8.33 (s, 1H), 9.18 (s, 1H).

EXAMPLE 17

4-(6-chloro-2,3-methylenedioxyanilino)-7-[2-(4-methylpiperazin-1-yl)ethoxy]-5-tetrahydropyran-4-yloxyquinazoline sesquifumarate salt A mixture of 4-(6-chloro-2,3-methylenedioxyanilino)-7-[2-(4-methylpiperazin-1-yl)ethoxy]-5-tetrahydropyran-4-yloxyquinazoline difumarate (0.15 g) and water (20 ml) was warmed using a heat gun to obtain a solution. The sample was allowed to evaporate slowly at ambient temperature to a volume of about 3 ml under a flow of air for 24 hours whereupon a precipitate had started to form. The mixture was placed in a refrigerator at 4° C. for 2 days. The resultant precipitate was isolated by filtration and washed with water. There was thus obtained 4-(6-chloro-2,3-methylenedioxyanilino)-7-[2-(4-methylpiperazin-1-yl)ethoxy]-5-tetrahydropyran-4-yloxyquinazoline as a sesquifumarate tetrahydrate salt (0.084 g) which was characterised using XRPD, DSC, TGA, FTIR and solution NMR techniques.

The invention claimed is:

1. A substantially homogeneous crystalline form of 4-(6-chloro-2,3-methylenedioxyanilino)-7-[2-(4-methylpiperazin-1-yl)ethoxy]-5-tetrahydropyran-4-yloxyquinazoline substantially in the form of a difumaric acid salt having an X-ray powder diffraction pattern with peaks at the following 2-theta values: 5.3, 7.1, 9.1, 10.6, 18.3, 19.3 and 21.1°, wherein said values may be plus or minus 0.3° 2-theta.

2. A substantially homogeneous crystalline form of 4-(6-chloro-2,3-methylenedioxyanilino)-7-[2-(4-methylpiperazin-1-yl)ethoxy]-5-tetrahydropyran-4-yloxyquinazoline substantially in the form of a trihydrate having an X-ray powder diffraction pattern with peaks at the following 2-theta values: 7.4, 13.8, 14.8, 16.0 and 17.8°, wherein said values may be plus or minus 0.3° 2-theta.

3. The substantially homogeneous crystalline form according to claim 1 wherein the degree of crystallinity is greater than about 60%.

4. The substantially homogeneous crystalline form according to claim 1 wherein the degree of crystallinity is greater than about 80%.

5. The substantially homogeneous crystalline form according to claim 1 wherein the degree of crystallinity is greater than about 90%.

6. The substantially homogeneous crystalline form according to claim 1 wherein the degree of crystallinity is greater than about 95%.

7. The substantially homogeneous crystalline form according to claim 1 wherein the molar ratio of each molecule of 4-(6-chloro-2,3-methylenedioxyanilino)-7-[2-(4-methylpiperazin-1-yl)ethoxy]-5-tetrahydropyran-4-yloxyquinazoline to each molecule of fumaric acid is in the range of 1:1.7 to 1:2.5.

8. The substantially homogeneous crystalline form according to claim 1 wherein the molar ratio of each molecule of 4-(6-chloro-2,3-methylenedioxyanilino)-7-[2-(4-methylpiperazin-1-yl)ethoxy]-5-tetrahydropyran-4-yloxyquinazoline to each molecule of fumaric acid is in the range of 1:1.8 to 1:2.3.

9. The substantially homogeneous crystalline form according to claim 1 wherein the molar ratio of each molecule of 4-(6-chloro-2,3-methylenedioxyanilino)-7-[2-(4-methylpiperazin-1-yl)ethoxy]-5-tetrahydropyran-4-yloxyquinazoline to each molecule of fumaric acid is in the range of 1:1.9 to 1:2.1.

10. The substantially homogeneous crystalline form according to claim 1 wherein the molar ratio of each molecule of 4-(6-chloro-2,3-methylenedioxyanilino)-7-[2-(4-methylpiperazin-1-yl)ethoxy]-5-tetrahydropyran-4-yloxyquinazoline to each molecule of fumaric acid is about 1:2.

11. A pharmaceutical composition which comprises the substantially homogeneous crystalline form of claim 1 and a pharmaceutically-acceptable diluent or carrier.

12. The substantially homogeneous crystalline form according to claim 2 wherein the degree of crystallinity is greater than about 90%.

13. The substantially homogeneous crystalline form according to claim 2 wherein the degree of crystallinity is greater than about 95%.

14. The substantially homogeneous crystalline form according to claim 2 wherein the molar ratio of each molecule of 4-(6-chloro-2,3-methylenedioxyanilino)-7-[2-(4-methylpiperazin-1-yl)ethoxy]-5-tetrahydropyran-4-yloxyquinazoline to each molecule of water is in the range of 1:2 to 1:4.

15. The substantially homogeneous crystalline form according to claim 2 wherein the molar ratio of each molecule of 4-(6-chloro-2,3-methylenedioxyanilino)-7-[2-(4-methylpiperazin-1-yl)ethoxy]-5-tetrahydropyran-4-yloxyquinazoline to each molecule of water is in the range of 1:2.5 to 1:3.5.

16. The substantially homogeneous crystalline form according to claim 2 wherein the molar ratio of each molecule of 4-(6-chloro-2,3-methylenedioxyanilino)-7-[2-(4-methylpiperazin-1-yl)ethoxy]-5-tetrahydropyran-4-yloxyquinazoline to each molecule of water is in the range of 1:2.75 to 1:3.25.

17. The substantially homogeneous crystalline form according to claim 2 wherein the molar ratio of each molecule of 4-(6-chloro-2,3-methylenedioxyanilino)-7-[2-(4-methylpiperazin-1-yl)ethoxy]-5-tetrahydropyran-4-yloxyquinazoline to each molecule of water is about 1:3.

18. A pharmaceutical composition which comprises the substantially homogeneous crystalline form of claim 2 and a pharmaceutically-acceptable diluent or carrier.

* * * * *